US008911721B2

(12) United States Patent
Shimatani et al.

(10) Patent No.: US 8,911,721 B2
(45) Date of Patent: Dec. 16, 2014

(54) METHOD OF CONSTRUCTING GENE TRANSPORT SUPPORT

(75) Inventors: Yuko Shimatani, Nagano (JP); Yoshinori Hamaji, Hyogo (JP); Hitomi Matsuhashi, Nagano (JP); Jun Amano, Nagano (JP); Shun'ichiro Taniguchi, Nagano (JP); Minoru Fujimori, Ibaraki (JP)

(73) Assignee: Anaeropharma Science, Inc., Tokyo (JP)

( * ) Notice: Subject to any disclaimer, the term of this patent is extended or adjusted under 35 U.S.C. 154(b) by 1130 days.

(21) Appl. No.: 12/301,670

(22) PCT Filed: May 24, 2007

(86) PCT No.: PCT/JP2007/060571
§ 371 (c)(1),
(2), (4) Date: Feb. 18, 2009

(87) PCT Pub. No.: WO2007/136107
PCT Pub. Date: Nov. 29, 2007

(65) Prior Publication Data
US 2009/0169516 A1    Jul. 2, 2009

(30) Foreign Application Priority Data

May 24, 2006 (JP) ................................. 2006-144720

(51) Int. Cl.
| A01N 63/00 | (2006.01) |
| C12N 1/20 | (2006.01) |
| C12N 15/74 | (2006.01) |
| A61K 31/513 | (2006.01) |
| A61K 35/74 | (2006.01) |
| C12N 9/78 | (2006.01) |
| A61K 48/00 | (2006.01) |

(52) U.S. Cl.
CPC ............. *A61K 48/0008* (2013.01); *A61K 48/00* (2013.01); *A61K 31/513* (2013.01); *A61K 35/745* (2013.01); *A61K 35/74* (2013.01); *C12N 9/78* (2013.01)
USPC ........................ 424/93.2; 435/252.3; 435/476

(58) Field of Classification Search
None
See application file for complete search history.

(56) References Cited

U.S. PATENT DOCUMENTS

| 6,416,754 B1 | 7/2002 | Brown et al. |
| 6,652,849 B2 | 11/2003 | Brown et al. |

FOREIGN PATENT DOCUMENTS

| EP | 1 829 963 A | 9/2007 |
| JP | 2002-097144 | 4/2002 |
| WO | WO 2006/109619 A1 | 10/2006 |

OTHER PUBLICATIONS

Argnani et al, 1996, Microbiology, 141:109-114.*
Lee and O'Sullivan, Applied and Environmental Microbiology, 2006, 72:527-535.*
Baneyx, Nature Biotechnology, 2004,22:1399-1408.*
Fujimori, Minoru, "Genetically engineered *Bifidobacterium* as a drug delivery system for synthetic therapy of metastatic breast cancer patients", Breast Cancer, JP Breast Cancer Sociey, Jan. 2006, vol. 13, No. 1, pp. 27-31.
Yazawa, et al., "*Bifidobacterium longum* as a delivery system for cancer gene therapy: Selective localization and growth in hypoxic tumors", Cancer Gene Therapy, 2000, vol. 7, No. 2, pp. 269-274.
Nakamura, et al., "Cloned Cytosine Deaminase Gene Expression of *Bifidobacterium longum* and Application to Enzyme/Pro-drug Therapy of Hypoxic Solid Tumors", Biosci. Biotechnol. Biochem., 2002, vol. 66, No. 11, pp. 2362-2366.
Mahan, et al., "Random Mutagenesis and Selection of *Escherichia coli* Cytosine Deaminase for Cancer Gene Therapy", Protein Eng. Des. & Sel., 2004. vol. 17, No. 8. pp. 625-633.
Takeuchi, et al., "Cloning and Expression in *Escherichia coli* of a Gene, *hup*, Encoding the Histone-like Protein HU of *Bifidobacterium longum*". Biosci. Biotechnol. Biochem., 2002. vol. 66, No. 3. pp. 598-603.
Fujimori et al., "The genis *Bifidobacterium* for cancer gene therapy," Current Opinion in Drug Discovery & Development, 2002, 5(2):200-203.
Matsumura et al., "Construction of *Escherichia coli-Bifidobacterium longum* Shuttle Vector Transforming *B. longum* 105-A and 108-A," Biosci. Biotech. Biochem., 1997, 61(7):1211-1212.
Tanaka et al., "Structural and Functional Analysis of pTB6 from *Bifidobacterium longum*," Biosci. Biotech. Biochem., 2005, 69(2):422-425.
Yazawa et al., "*Bifidobacterium longum* as a delivery system for gene therapy of chemically induced rat mammary tumors," Breast Cancer Research and Treatment, 2001, 66:165-170.

* cited by examiner

*Primary Examiner* — Valarie Bertoglio
(74) *Attorney, Agent, or Firm* — Foley & Lardner LLP

(57) ABSTRACT

An object of the present invention is to provide a method of efficiently constructing a gene delivery carrier having a favorable activity and expression efficiency of a protein expressed by a gene introduced by transformation. Moreover, an object of the present invention is to provide a pharmaceutical composition comprising a gene delivery carrier constructed by the construction method and a therapeutic agent for solid tumor comprising the resistant bacterium. The objects of the present invention have been attained by a gene delivery carrier consisting of an anaerobic microorganism capable of growing in a tumor tissue in an anaerobic environment and capable of expressing (A) a protein having an antitumor activity or (B) a protein having an activity of converting an antitumor substance precursor to an antitumor substance, wherein DNA encoding the protein of interest is allowed to further comprise, on the 5'-terminal side thereof, a DNA fragment comprising a nucleotide sequence encoding a peptide consisting of an amino acid sequence from the 1st to at least 4th amino acids at the N-terminus of a histone-like DNA-binding protein.

15 Claims, 3 Drawing Sheets

METHOD OF CONSTRUCTING GENE TRANSPORT SUPPORT

This application is the National Stage of International Application No. PCT/JP2007/060571, filed May 24, 2007, which claims the benefit of Japanese Patent Application No. 2006-144720, filed May 24, 2006, each of which is hereby incorporated by reference in its entirety.

TECHNICAL FIELD

The present invention relates to a method of constructing a gene delivery carrier consisting of an anaerobic microorganism capable of growing in a tumor tissue in an anaerobic environment and capable of expressing (A) a protein having an antitumor activity or (B) a protein having an activity of converting an antitumor substance precursor to an antitumor substance, which is useful as a therapeutic agent for solid tumor. Moreover, the present invention relates to a pharmaceutical composition comprising a gene delivery carrier constructed by the method and to a therapeutic agent for solid tumor comprising the gene delivery carrier.

BACKGROUND ART

In recent years, therapies for malignant tumor using a gene delivery carrier have been studied in various ways. For example, with regard to an anaerobic bacterium *Clostridium*, a method of transporting a gene to a tumor site using a transformed bacterium has been proposed (see e.g., Patent Documents 1 and 2).

Likewise, with regard to an anaerobic bacterium *Bifidobacterium*, its transformant has been expected to be applied as a vector for probiotics or a vector for an oral vaccine for infectious disease (see e.g., Patent Document 3). Moreover, with regard to *Bifidobacterium longum*, its application to treatment of solid tumor has been suggested, because this bacterium accumulates in hypoxic solid tumor after systemic administration (see e.g., Non-Patent Documents 1 and 2).

Moreover, the present inventors have confirmed that, by transformation with a recombinant plasmid pBLES100-S-eCD carrying *Escherichia coli* coda fused with a promoter of a histone-like DNA-binding protein derived from *Bifidobacterium longum*, cytosine deaminase (EC3.5.4.1; hereinafter, referred to as "CD") which is an enzyme that converts 5-fluorocytosine (hereinafter, referred to as "5-FC") as a prodrug (precursor) of 5-fluorouracil (hereinafter, referred to as "5-FU") having an antitumor activity, to 5-fluorouracil, can be expressed in a recombinant microorganism, and have reported that the recombinant microorganism, for example, recombinant *Bifidobacterium longum*, can be expected to be applied to enzyme-prodrug therapies (see e.g., Patent Document 4 and Non-Patent Documents 3 and 4). For applying this CD-expressing genetically modified microorganism to enzyme-prodrug therapies, it is further required that the microorganism should have a resistance to 5-FU at a concentration at least effective for an antitumor activity, which is converted from 5-FC by CD. Therefore, the present inventors have developed and reported a method of constructing such a CD-expressing 5-FU-resistant bacterium (see e.g., Patent Document 5). On the other hand, with regard to this CD, Non-Patent Document 5 has reported that when a mutation that substituted aspartic acid by alanine at the 314th (corresponding to the 315th position in SEQ ID NO: 28 of the present invention) amino acid of CD was added to CD-encoding DNA in *Escherichia coli*, mutant CD had a CD activity of converting 5-FC to 5-FU that was approximately 2.2 times (50/23) higher than that of wild-type CD before mutation (see the middle section of Table 1 in Non-Patent Document 5).

Various transformation methods have been reported on recombinant bacteria used in treatment of malignant tumor. In the documents described above, their respective methods of preparing a transformed bacterium have been reported.

For example, Patent Document 3 has reported a transformation method comprising the steps of: producing a shuttle plasmid that is mutually replicated in both *Bifidobacterium* species and *Escherichia coli*, using a *Bifidobacterium* species-derived plasmid and an *Escherichia coli*-derived plasmid; and producing a recombinant vector by ligating a gene of interest encoding a protein of interest to the shuttle plasmid, wherein the *Bifidobacterium* species used in the production of the shuttle plasmid is used as a host cell to be transformed with the produced recombinant vector.

In addition, for example, with regard to a method of preparing a shuttle plasmid pBLES100 used in the construction of the recombinant plasmid pBLES100-S-eCD, a preparation method comprising constructing this shuttle plasmid from pTB6 of *Bifidobacterium longum* BK51 and pBR322 of *Escherichia coli* has been reported (see e.g., Non-Patent Document 6).

Furthermore, methods of preparing plasmids pAV001 and pBRASTA101 have been proposed, which are capable of transforming *Bifidobacterium longum* with 100 times or higher efficiency than that of the shuttle plasmid pBLES100 (see e.g., Non-Patent Document 7).

Thus, various methods of constructing a gene delivery carrier useful for treatment of malignant tumor have been reported. However, all of these methods have specified microorganisms, plasmids, or the like used in transformation and have used usual transformation techniques as a transformation method itself. Moreover, these methods are intended to construct a transformed microorganism itself capable of expressing, in a target affected area, a gene of interest, for example, a gene for expressing a protein having an antitumor activity or a protein having an activity of converting an antitumor substance precursor to an antitumor substance. No documents has reported so far a construction method that is intended to improve the activity or expression efficiency of a protein itself expressed from the gene of interest.

Patent Document 1: U.S. Pat. No. 6,416,754
Patent Document 2: U.S. Pat. No. 6,652,849
Patent Document 3: National Publication of International Patent Application No. 2004-519236
Patent Document 4: Japanese Patent Laid-Open No. 2002-97144
Patent Document 5: WO 2006/109619
Non-Patent Document 1: Yazawa et al. Cancer Gene Ther., 7, 269-274 (2000)
Non-Patent Document 2: Yazawa et al. Breast Cancer Res. Treat., 66, 165-170 (2001)
Non-Patent Document 3: Nakamura et al., Biosci. Biotechnol. Biochem., 66, 2362-2366 (2002)
Non-Patent Document 4: Fujimori et al., Curr. Opin. Drug Discov. Devel., 5, 200-203 (2002)
Non-Patent Document 5: Sheri et al., Protein Engineering, Design and Selection, 17 (8): 625-633 (2004)
Non-Patent Document 6: Matsumura et al., Biosci. Biotechnol. Biochem., 61, 1211-1212 (1997)
Non-Patent Document 7: Tanaka et al., Biosci Biotechnol Biochem.; 69 (2): 422-425 (2005)

DISCLOSURE OF THE INVENTION

Object to be Solved by the Invention

All of previously reported methods of constructing a gene delivery carrier useful for the treatment of malignant tumor are intended to construct a transformed bacterium itself capable of expressing, in a target affected area, a gene of interest, for example, a gene for expressing a protein having an antitumor activity or a protein having an activity of converting an antitumor substance precursor to an antitumor substance. No documents has reported so far a construction method that is intended to improve the activity or expression efficiency of a protein itself expressed from the gene of interest.

However, for therapies using a gene delivery carrier, the activity and expression efficiency of a protein expressed by a gene introduced in a transformed microorganism are important issues. It is naturally required that the protein expressed by a gene in the transformed microorganism should have the same activity as that of a protein expressed by a gene carried by the original wild-type microorganism and, furthermore, should be expressed at a level equal to or more than that by the gene carried by the original microorganism.

An object of the present invention is to provide a method of efficiently constructing a gene delivery carrier having a favorable activity and expression efficiency of a protein expressed by a gene introduced by transformation. Moreover, an object of the present invention is to provide a pharmaceutical composition comprising a gene delivery carrier constructed by the construction method and a therapeutic agent for solid tumor comprising the resistant bacterium.

Means for Solving the Problems

The present inventors have selected beforehand, as a gene of interest, a gene expressing CD among proteins having an activity of converting an antitumor substance precursor to an antitumor substance, and have constructed, as a plasmid to which the gene of interest is incorporated, a plasmid pBLES100-S-eCD comprising a plasmid of *Escherichia coli* carrying the gene for expressing CD and a *Bifidobacterium longum*-derived plasmid fused therewith. The present inventors have found that *Bifidobacterium longum* 105A/pBLES100-S-eCD obtained by genetically modifying *Bifidobacterium longum* 105A with this plasmid can be expected as a gene delivery carrier useful for treatment of malignant tumor, and have reported a construction method thereof comprising, in the step of constructing the gene expression vector by incorporation of the gene of interest, using a promoter involved in expression of a gene encoding a histone-like DNA-binding protein (hereinafter, also referred to as an "HU protein") derived from *Bifidobacterium longum* and incorporating the gene of interest downstream of the promoter to thereby construct a transformed microorganism capable of expressing the gene of interest (Patent Document 4).

The present inventors have further conducted diligent studies on the above method, and have found that a transformation frequency can be enhanced by using, as a fusion plasmid to which the gene of interest is incorporated, a plasmid prepared by fusing *Escherichia coli*-derived and *Bifidobacterium longum*-derived plasmid fragments that contain portions essential for their plasmid replications and contain no portions unfavorable for expansion of a host range.

Moreover, the present inventors have found that for incorporating the gene of interest downstream of the promoter involved in expression of a gene encoding a histone-like DNA-binding protein of the microorganism used as a host, it is required that the gene of interest should have, on the 5'-terminal side thereof, a DNA fragment encoding an N-terminal region of the histone-like DNA-binding protein, and that it is further required that the DNA fragment should comprise a DNA fragment encoding at least 4 amino acids.

Specifically, the present inventors have found that for incorporating the gene of interest downstream of the promoter involved in expression of a gene encoding the histone-like DNA-binding protein, a DNA fragment comprising a nucleotide sequence encoding an amino acid sequence from the 1st to at least 4th amino acids at the N-terminus of the histone-like DNA-binding protein can be incorporated on the 5'-terminal side of DNA of the gene of interest to thereby construct a microorganism capable of expressing a protein having the same activity as that of the gene product (protein) in a microorganism used as a source of the gene of interest, at a level equal to or more than that by the microorganism used as a source of the gene of interest.

The present inventors have further found that a protein having a higher activity can be produced by partially mutating DNA of the gene of interest incorporated in the step of expression vector preparation. Furthermore, the present inventors have also found that particularly when the gene of interest is a gene for expressing CD among proteins having an activity of converting an antitumor substance precursor to an antitumor substance, a genetically modified microorganism having a high plasmid retention rate can be constructed by using, as an anaerobic microorganism used as a host, a 5-fluorouracil-resistant bacterium having a resistance to 5-fluorouracil at a concentration at least effective for an antitumor activity. As a result, the present invention has been completed.

Specifically, the present invention relates to:

[1] a method of constructing a gene delivery carrier consisting of an anaerobic microorganism capable of growing in a tumor tissue in an anaerobic environment and capable of expressing (A) a protein having an antitumor activity or (B) a protein having an activity of converting an antitumor substance precursor to an antitumor substance, comprising the steps of:

(1) preparing a fusion plasmid having a fragment of a plasmid of a bacterium of the genus *Bifidobacterium* and a fragment of a plasmid of *Escherichia coli*;

(2) incorporating, a DNA fragment comprising a promoter and a terminator of a gene encoding a histone-like DNA-binding protein derived from a bacterium of the genus *Bifidobacterium* to the fusion plasmid;

(3) incorporating, between the promoter and the terminator, (a) a DNA encoding a protein having an antitumor activity or (b) a DNA encoding a protein having an activity of converting an antitumor substance precursor to an antitumor substance to prepare an expression vector; and (4) transforming an anaerobic microorganism with the expression vector, wherein (a) the DNA encoding a protein having an antitumor activity or (b) the DNA encoding a protein having an activity of converting an antitumor substance precursor to an antitumor substance, which is incorporated in the step (3) of expression vector preparation, further comprises on the 5'-terminal side thereof, a DNA fragment comprising a nucleotide sequence encoding a peptide consisting of an amino acid sequence from the 1st to at least 4th amino acids at the N-terminus of the histone-like DNA-binding protein;

[2] the method of constructing a gene delivery carrier according to [1], wherein the peptide consisting of an amino acid sequence from the 1st to at least 4th amino acids at the N-terminus of the histone-like DNA-binding protein is a peptide consisting of an amino acid sequence from the 1st amino acid to any one of the 4th to 18th amino acids in SEQ ID NO: 29;

[3] the method of constructing a gene delivery carrier according to [1] or [2], further comprising before the step (4), a step (5) of mutating (a) the DNA encoding a protein having an antitumor activity or (b) the DNA encoding a protein having an activity of converting an antitumor substance precursor to an antitumor substance;

[4] the method of constructing a gene delivery carrier according to [3], wherein the step (5) of mutating (a) the DNA encoding a protein having an antitumor activity or (b) the DNA encoding a protein having an activity of converting an antitumor substance precursor to an antitumor substance is a step (5') of mutating (a) the DNA encoding a protein having an antitumor activity or (b) the DNA encoding a protein having an activity of converting an antitumor substance precursor to an antitumor substance, which has been incorporated in the expression vector prepared in the step (3);

[5] the method of constructing a gene delivery carrier according to any one of [1] to [4], wherein the gene delivery carrier is a gene delivery carrier consisting of an anaerobic microorganism capable of growing in a tumor tissue in an anaerobic environment and capable of expressing a protein having an activity of converting an antitumor substance precursor to an antitumor substance;

[6] the method of constructing a gene delivery carrier according to any one of [1] to [5], wherein the protein having an activity of converting an antitumor substance precursor to an antitumor substance is cytosine deaminase;

[7] the method of constructing a gene delivery carrier according to [6], wherein the gene delivery carrier consisting of an anaerobic microorganism is a cytosine deaminase-expressing 5-fluorouracil-resistant bacterium having a resistance to 5-fluorouracil at a concentration at least effective for an antitumor activity;

[8] the method of constructing a gene delivery carrier according to [7], wherein the cytosine deaminase-expressing 5-fluorouracil-resistant bacterium having a resistance to 5-fluorouracil at a concentration at least effective for an antitumor activity is prepared using, a 5-fluorouracil-resistant bacterium having a resistance to 5-fluorouracil at a concentration at least effective for an antitumor activity as a host;

[9] the method of constructing a gene delivery carrier according to any one of [1] to [8], wherein the DNA fragment comprising a nucleotide sequence encoding a peptide consisting of an amino acid sequence from the 1st to at least 4th amino acids at the N-terminus of the histone-like DNA-binding protein is a DNA fragment comprising a nucleotide sequence from the 1482nd to at least 1493rd nucleotides in SEQ ID NO: 14 or 15;

[10] the method of constructing a gene delivery carrier according to [9], wherein the DNA fragment comprising a nucleotide sequence from the 1482nd to at least 1493rd nucleotides in SEQ ID NO: 14 or 15 is a DNA fragment comprising a nucleotide sequence from the 1482nd nucleotide to any one of the 1493rd to 1535th nucleotides in SEQ ID NO: 15;

[11] the method of constructing a gene delivery carrier according to any one of [1] to [10], wherein the anaerobic microorganism is a bacterium;

[12] the method of constructing a gene delivery carrier according to [11], wherein the bacterium is an enteric bacterium;

[13] the method of constructing a gene delivery carrier according to [12], wherein the enteric bacterium is a bacterium of the genus *Bifidobacterium*;

[14] the method of constructing a gene delivery carrier according to [13], wherein the bacterium of the genus *Bifidobacterium* is any bacterium of the genus *Bifidobacterium* selected from *Bifidobacterium adolescentis*, *Bifidobacterium animalis*, *Bifidobacterium infantis*, *Bifidobacterium thermophilum*, *Bifidobacterium pseudolongum*, *Bifidobacterium bifidum*, *Bifidobacterium breve*, and *Bifidobacterium longum*;

[15] the method of constructing a gene delivery carrier according to [13] or [14], wherein the bacterium of the genus *Bifidobacterium* is *Bifidobacterium longum*;

[16] the method of constructing a gene delivery carrier according to any one of [1] to [15], wherein the expression vector used in the transformation in the step (4) is a single-nucleotide mutation-introduced plasmid of a plasmid pAV001-HU-eCD;

[17] the method of constructing a gene delivery carrier according to [16], wherein a CD-encoding nucleotide sequence in the single-nucleotide mutation-introduced plasmid of a plasmid pAV001-HU-eCD is a nucleotide sequence encoding an amino acid sequence in which aspartic acid as an amino acid corresponding to the 315th position in an *Escherichia coli* CD amino acid sequence described in SEQ ID NO: 28 has been substituted by another amino acid;

[18] the method of constructing a gene delivery carrier according to [17], wherein the another amino acid is alanine; and

[19] the method of constructing a gene delivery carrier according to [18], wherein the single-nucleotide mutation-introduced plasmid of a plasmid pAV001-HU-eCD is a plasmid pAV001-HU-eCD-M968.

Moreover, the present invention relates to:

[20] a gene delivery carrier consisting of an anaerobic microorganism transformed with an expression vector having a fragment of a plasmid of a bacterium of the genus *Bifidobacterium*, a fragment of a plasmid of *Escherichia coli*, and a DNA fragment comprising a promoter and a terminator of a gene encoding a histone-like DNA-binding protein derived from a bacterium of the genus *Bifidobacterium*, having, between the promoter and the terminator, (a) a DNA encoding a protein having an antitumor activity or (b) a DNA encoding a protein having an activity of converting an antitumor substance precursor to an antitumor substance, and further comprising a DNA fragment comprising a nucleotide sequence encoding a peptide consisting of an amino acid sequence from the 1st to at least 4th amino acids at the N-terminus of the histone-like DNA-binding protein, on the 5'-terminal side of (a) the DNA encoding a protein having an antitumor activity or (b) the DNA encoding a protein having an activity of converting an antitumor substance precursor to an antitumor substance;

[21] a gene delivery carrier consisting of an anaerobic microorganism being capable of growing in a tumor tissue in an anaerobic environment and having (a) a DNA encoding a protein having an antitumor activity or (b) a DNA encoding a protein having an activity of converting an antitumor substance precursor to an antitumor substance, the gene delivery carrier being constructed by the construction method according to any one of [1] to [19];

[22] the gene delivery carrier according to [20] or [21], wherein the anaerobic bacterium is a bacterium of the genus *Bifidobacterium*;

[23] the gene delivery carrier according to [22], wherein the bacterium of the genus *Bifidobacterium* is any bacterium of the genus *Bifidobacterium* selected from *Bifidobacterium adolescentis*, *Bifidobacterium animalis*, *Bifidobacterium infantis*, *Bifidobacterium thermophilum*, *Bifidobacterium*

*pseudolongum, Bifidobacterium bifidum, Bifidobacterium breve*, and *Bifidobacterium longum;*

[24] the gene delivery carrier according to [22] or [23], wherein the bacterium of the genus *Bifidobacterium* is *Bifidobacterium longum;*

[25] the gene delivery carrier according to any one of [20] to [24], wherein the gene delivery carrier is capable of growing in a tumor tissue in an anaerobic environment and is capable of expressing a protein having an activity of converting an antitumor substance precursor to an antitumor substance;

[26] the gene delivery carrier according to [25], wherein the protein having an activity of converting an antitumor substance precursor to an antitumor substance is cytosine deaminase;

[27] the gene delivery carrier according to [26], wherein the gene delivery carrier is a cytosine deaminase-expressing 5-fluorouracil-resistant bacterium having a resistance to 5-fluorouracil at a concentration at least effective for an antitumor activity;

[28] the gene delivery carrier according to [26] or [27], wherein the gene delivery carrier is a single-nucleotide mutant plasmid of *Bifidobacterium longum* 105A/pAV001-HU-eCD; and

[29] the gene delivery carrier according to [28], wherein the single-nucleotide mutant plasmid of *Bifidobacterium longum* 105-A/pAV001-HU-eCD is *Bifidobacterium longum* 105-A/pAV001-HU-eCD-M968.

Furthermore, the present invention relates to:

[30] a pharmaceutical composition comprising the gene delivery carrier according to any one of [20] to [29];

[31] a pharmaceutical composition comprising the gene delivery carrier according to any one of [25] to [29] in combination with an antitumor substance precursor converted to an antitumor substance by the protein capable of being expressed by the gene delivery carrier; and

[32] the pharmaceutical composition according to [31], wherein the gene delivery carrier is the gene delivery carrier according to any one of [25] to [29], and the antitumor substance precursor is 5-fluorocytosine.

Furthermore, the present invention also relates to:

[33] a therapeutic agent for solid tumor comprising the gene delivery carrier according to any one of [20] to [24] in an amount sufficient for expression of a therapeutically effective amount of a protein having an antitumor activity;

[34] a therapeutic agent for solid tumor comprising the gene delivery carrier according to any one of [25] to [29] in an amount sufficient for expression of the protein in an amount capable of converting an antitumor substance precursor to a therapeutically effective amount of an antitumor substance, in combination with an antitumor substance precursor converted by the protein capable of being expressed by the gene delivery carrier, in an amount capable of being converted to a therapeutically effective amount of an antitumor substance; and

[35] the therapeutic agent for solid tumor according to [34], wherein the gene delivery carrier is the gene delivery carrier according to any one of [25] to [29], and the antitumor substance precursor is 5-fluorocytosine.

In the present specification, (a) the DNA encoding a protein having an antitumor activity or (b) the DNA encoding a protein having an activity of converting an antitumor substance precursor to an antitumor substance is also hereinafter referred to as "DNA encoding the protein of interest".

According to the present invention, a gene delivery carrier consisting of an anaerobic microorganism an anaerobic microorganism capable of growing in a tumor tissue in an anaerobic environment and capable of expressing a protein having an antitumor activity or a protein having an activity of converting an antitumor substance precursor to an antitumor substance, which is useful as a therapeutic agent for solid tumor and has a favorable activity and expression efficiency of a protein expressed by a gene introduced by transformation, can be constructed efficiently.

By administration of the gene delivery carrier according to the present invention to a patient with malignant tumor or the like, the anaerobic microorganism as the gene delivery carrier of the present invention proliferates in the tumor and expresses the protein of interest therein. When the protein of interest is a protein having an antitumor activity, the protein directly exhibits its antitumor effect. On the other hand, when the protein of interest is a protein having an activity of converting an antitumor substance precursor to an antitumor substance, the protein of interest expressed from the gene delivery carrier converts an antitumor substance precursor to an antitumor substance in the coexistence of the gene delivery carrier and the antitumor substance precursor in the tumor site, and the antitumor substance exhibits its antitumor effect.

When the protein having an activity of converting an antitumor substance precursor to an antitumor substance is CD, 5-FC is preferably used as an antitumor substance precursor. 5-FC is converted to 5-FU by CD, and this 5-FU exhibits an excellent antitumor effect. Systemic administration of 5-FU in an amount that produces a sufficient antitumor effect by the systemic administration causes systemic side effects. However, the use of the gene delivery carrier of the present invention can convert 5-FC with few side effects to 5-FU in a manner specific for a tumor site. Therefore, it can achieve a much higher 5-FU concentration in the tumor than that achieved by direct administration of 5-FU. As a result, an extremely excellent antitumor effect is obtained.

However, only the conversion of 5-FC to 5-FU in a tumor site using a CD-expressing gene delivery carrier is not sufficient for obtaining a therapeutic agent for tumor at a level that can be readily put into practical use. The antitumor effect or practicality of such a therapeutic agent for tumor largely depends on three factors: the level of cells of an anaerobic microorganism as a gene delivery carrier; the degree of a CD activity exhibited by the anaerobic microorganism; and the concentration of 5-FC in a tumor site. Larger the doses of 5-FC and the anaerobic microorganism are, stronger the obtained antitumor effect naturally becomes. From the viewpoint of minimizing side effects, it is preferred that the dose of 5-FC should be reduced as much as possible within a range that produces a necessary antitumor effect. It is at least required that the dose should be lower than clinically acceptable one. Moreover, even if an anaerobic microorganism with lowest toxicity is used, it is preferred from the viewpoint of minimizing the influence on human bodies that its dose should be reduced as much as possible within a range that produces a necessary antitumor effect. In consideration of these situations, none of conventional antitumor agents that use the conversion of 5-FC to 5-FU in a tumor site using a CD-expressing gene delivery carrier had sufficient practicality at a clinical level.

For example, in Example 4 in Patent Document 4, a 5-FC concentration used in treatment experiments using mice was 500 mg/kg, and an effective and sufficient antitumor effect was obtained at the concentration. However, as can be seen from the description "for fungemia, fungal meningitis, mycotic respiratory infection, and chromomycosis, this drug is usually orally administered at four divided doses of 100 to 200 mg/kg/day as fluorocytosine; for urinary tract mycosis and digestive tract mycosis, this drug is usually orally administered at four divided doses of 50 to 100 mg/kg/day as fluorocytosine" for the dosage and administration of a therapeutic agent ANCOTIL (containing 500 mg of flucytosine described in the Japanese Pharmacopoeia) for deep mycosis from Kyowa Pharmaceutical Industry, Co., Ltd., the maximum dose of 5-FC actually acceptable in clinical tests is 200 mg/kg. Thus, for obtaining a sufficient antitumor effect at the clinical dose (200 mg/kg) of 5-FC using the experimental system used in Example in Patent Document 4, an at least 2.5-fold (≈500/200) higher enzyme activity was required.

On the other hand, Non-Patent Document 5 has reported that when a mutation that substituted aspartic acid by alanine at the 314th (corresponding to the 315th position in SEQ ID NO: 28 of the present invention) amino acid of CD was added to CD-encoding DNA in *Escherichia coli*, mutant CD had a CD activity (kcat/Km value) of converting 5-FC to 5-FU that was approximately 2.2 times (50/23) higher than that of wild-type CD before mutation. This enhanced effect of producing the higher activity is still insufficient for attaining the objects. However, in the gene delivery carrier of the present invention, DNA encoding CD as the protein of interest was allowed to further comprise, on the 5'-terminal side thereof, a DNA fragment comprising a nucleotide sequence encoding a peptide consisting of an amino acid sequence from the 1st to at least 4th amino acids at the N-terminus of the histone-like DNA-binding protein, and the aspartic acid at the 315th position in SEQ ID NO: 28 of the CD was substituted by alanine. As a result, totally unexpectedly, the CD activity that was even approximately 12-fold higher was obtained.

From this 12-fold higher CD activity, the 5-FC dose was calculated to be approximately 42 mg/kg, with respect to the experimental results described above. This means that the minimum clinical dose (50 mg/kg) or lower is enough. Thus, extremely high practicality can be expected.

Thus, among the gene delivery carriers of the present invention, the gene delivery carrier (e.g., *Bifidobacterium longum* 105-A/pAV001-HU-eCD-M968) of the present invention, wherein DNA encoding CD as the protein of interest is allowed to further comprise, on the 5'-terminal side thereof, a DNA fragment comprising a nucleotide sequence encoding a peptide consisting of an amino acid sequence from the 1st to at least 4th amino acids at the N-terminus of the histone-like DNA-binding protein, and the aspartic acid at the 315th position in SEQ ID NO: 28 of the CD has been substituted by alanine, can particularly be expected to have excellent practicality.

Indeed, it has been confirmed that when a unmutated CD-expressing gene delivery carrier (recombinant *Bifidobacterium longum*) used in Patent Document 4 is used in a treatment system using human-derived breast cancer cell line (KPL-1)-transplanted nude mice, a bacterial concentration required for converting 5-FC to an effective concentration of 5-FU in the tumor is $10^7$ CFU/g or more. It has been confirmed by the experiments of the present inventors that when the gene delivery carrier of the present invention, wherein the aspartic acid at the 315th position in SEQ ID NO: 28 of the CD has been substituted by alanine, is used in the same experimental system, an equivalent 5-FU concentration in the tumor is obtained at a bacterial concentration of $10^5$ CFU/g, which is 1/100 of the bacterial concentration described above.

BEST MODE OF CARRYING OUT THE INVENTION

Figure 1:
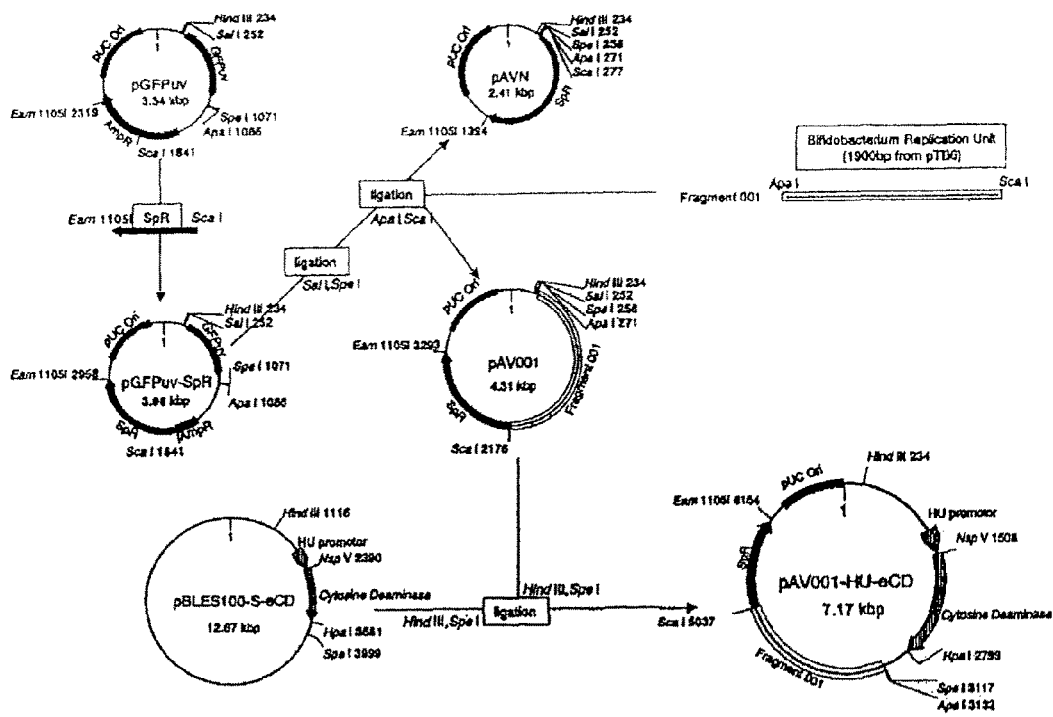
FIG. 1
It is a diagram showing the process of preparing *Bifidobacterium longum* 105A/pAV001-HU-eCD.

A method of constructing a gene delivery carrier according to the present invention is a method of constructing a gene delivery carrier consisting of an anaerobic microorganism capable of growing in a tumor tissue in an anaerobic environment and capable of expressing (A) a protein having an antitumor activity or (B) a protein having an activity of converting an antitumor substance precursor to an antitumor substance, comprising the steps of:

(1) preparing a fusion plasmid having a fragment of a plasmid of a bacterium of the genus *Bifidobacterium* and a fragment of a plasmid of *Escherichia coli*;

(2) incorporating, a DNA fragment comprising a promoter and a terminator of a gene encoding a histone-like DNA-binding protein derived from a bacterium of the genus *Bifidobacterium* to the fusion plasmid;

(3) incorporating, between the promoter and the terminator, (a) a DNA encoding a protein having an antitumor activity or (b) a DNA encoding a protein having an activity of converting an antitumor substance precursor to an antitumor substance to prepare an expression vector; and (4) transforming an anaerobic microorganism with the expression vector, wherein (a) the DNA encoding a protein having an antitumor activity or (b) the DNA encoding a protein having an activity of converting an antitumor substance precursor to an antitumor substance, which is incorporated in the step (3) of expression vector preparation, further comprises on the 5'-terminal side thereof, a DNA fragment comprising a nucleotide sequence encoding a peptide consisting of an amino acid sequence from the 1st to at least 4th amino acids at the N-terminus of the histone-like DNA-binding protein.

The method of constructing a gene delivery carrier according to the present invention is not particularly limited as long as it comprises the steps of: (1) preparing a fusion plasmid having a fragment of a plasmid of a bacterium of the genus *Bifidobacterium* and a fragment of a plasmid of *Escherichia coli*; (2) incorporating, a DNA fragment comprising a promoter and a terminator of a gene encoding a histone-like DNA-binding protein derived from a bacterium of the genus *Bifidobacterium* to the fusion plasmid; (3) incorporating, between the promoter and the terminator, (a) a DNA encoding a protein having an antitumor activity or (b) a DNA encoding a protein having an activity of converting an antitumor substance precursor to an antitumor substance to prepare an expression vector; and (4) transforming an anaerobic microorganism with the expression vector, wherein (a) the DNA encoding a protein having an antitumor activity or (b) the DNA encoding a protein having an activity of converting an antitumor substance precursor to an antitumor substance, which is incorporated in the step (3) of expression vector preparation, further comprises on the 5'-terminal side thereof, a DNA fragment comprising a nucleotide sequence encoding a peptide consisting of an amino acid sequence from the 1st to at least 4th amino acids at the N-terminus of the histone-like DNA-binding protein.

The method of constructing a gene delivery carrier according to the present invention is not particularly limited as long as it comprises the steps (1) to (4). It may additionally comprise an arbitrary step unless the effects of the present invention are impaired. Moreover, in the method of constructing a gene delivery carrier according to the present invention, the order in which the steps (2) and (3) are performed is not particularly limited. It may comprise these steps in the order of the steps (1), (2), (3), and (4) or may comprise these steps in the order of the steps (1), (3), (2), and (4). Both of these aspects are encompassed in the method of constructing a gene delivery carrier according to the present invention for convenience.

Particularly, for incorporating the DNA encoding the protein of interest in the step (3) of expression vector preparation, the aspect of allowing the DNA encoding the protein of interest to comprise on the 5'-terminal side thereof, a DNA fragment encoding the N-terminal region of the HU protein may be any aspect. It may be, for example, an aspect of adding the DNA fragment encoding the N-terminal region of the HU protein to the 5'-terminal side of the DNA encoding the protein of interest, to thereby incorporate the DNA fragment therein, or may be an aspect of incorporating the DNA encoding the protein of interest to the intermediate position of DNA encoding the HU protein such that the DNA encoding the protein of interest is sandwiched between DNA encoding the N-terminal region of the HU protein and DNA encoding the C-terminal region of the HU protein.

The order in which in the step (3) of expression vector preparation, the DNA encoding the protein of interest is allowed to comprise, on the 5'-terminal side thereof, a DNA fragment encoding the N-terminal region of the HU protein is not particularly limited as long as an expression vector comprising the DNA fragment encoding the N-terminal region of the HU protein on the 5'-terminal side of the DNA encoding the protein of interest is obtained. For example, after allowing the DNA encoding the protein of interest to comprise, on the 5'-terminal side thereof, the DNA fragment encoding the N-terminal region of the HU protein, the resulting DNA may be incorporated to the fusion plasmid. Alternatively, after incorporating the DNA encoding the protein of interest to the fusion plasmid, the DNA fragment encoding the N-terminal region of the HU protein may be incorporated to the 5'-terminal side of the DNA encoding the protein of interest. Or otherwise, after incorporating the DNA fragment encoding the N-terminal region of the HU protein to the fusion plasmid, the DNA encoding the protein of interest may be incorporated to the 3'-terminal side of the DNA fragment encoding the N-terminal region of the HU protein.

Moreover, the 3'-terminus of the DNA fragment encoding the N-terminal region of the HU protein and the 5'-terminus of the DNA encoding the protein of interest do not have to be bonded directly in the expression vector according to the present invention as long as the effects of the present invention are obtained. However, it is preferred that they are bonded directly.

In this case, if the DNA fragment encoding the N-terminal region of the HU protein, which is comprised on the 5'-terminal side of the DNA encoding the protein of interest, is too long, the nature of the protein of interest expressed might be altered. Therefore, from this viewpoint, it is preferred that the DNA fragment encoding the N-terminal region of the HU protein is as short as possible. However, if the DNA fragment encoding the N-terminal region of the HU protein is too short, the expression rate of the protein is reduced. Therefore, from both of these viewpoints, it is preferred that the DNA fragment encoding the N-terminal region of the HU protein has a well-balanced moderate length.

Specifically, the DNA fragment encoding the N-terminal region of the HU protein is not particularly limited as long as it is a DNA fragment comprising a nucleotide sequence encoding a peptide consisting of an amino acid sequence from the 1st to at least 4th amino acids at the N-terminus of the HU protein. It is preferred that the DNA fragment encoding the N-terminal region of the HU protein is a DNA fragment comprising a nucleotide sequence encoding a peptide consisting of an amino acid sequence from the 1st amino acid to any one of the 4th to 18th amino acids at the N-terminus of the HU protein. The amino acid sequence from the 1st to 18th amino acids at the N-terminus of the HU protein is described in SEQ ID NO: 29. The amino acid sequence of SEQ ID NO: 29 is an amino acid sequence encoded by a nucleotide sequence from the 1482nd to 1535th nucleotides in SEQ ID NO: 15.

Examples of a plasmid having a DNA fragment comprising a nucleotide sequence encoding a peptide consisting of an amino acid sequence from the 1st to 4th amino acids at the N-terminus of the HU protein can include pAV001-HU4aa-eCD (SEQ ID NO: 14). Examples of a plasmid having a DNA fragment comprising a nucleotide sequence encoding a peptide consisting of an amino acid sequence from the 1st to 9th amino acids at the N-terminus of the HU protein can include pAV001-HU-eCD (pAV001-HU9aa-eCD). Examples of a plasmid having a DNA fragment comprising a nucleotide sequence encoding a peptide consisting of an amino acid sequence from the 1st to 18th amino acids at the N-terminus of the HU protein can include pAV001-HU18aa-eCD (SEQ ID NO: 15).

A method of changing the length of the N-terminal region of the HU protein is not particularly limited. As performed in Examples described later, appropriate primers are designed based on the sequence of the N-terminal region of the HU protein, and the sequence of an N-terminal region having the desired number of amino acids can be obtained easily by PCR or the like using those primers.

Moreover, the construction method of the present invention is a construction method using, a fusion plasmid having a fragment of a plasmid of a bacterium of the genus *Bifidobacterium* and a fragment of a plasmid of *Escherichia coli* in the step (1). The fragment of a plasmid of a bacterium of the genus *Bifidobacterium* used in the present invention is preferably a fragment of a plasmid derived from *Bifidobacterium longum*. Examples thereof can include portions of pTB6-derived regions containing a pTB6 replication origin (oriV) (base Nos. 3419 to 3778 of SEQ ID NO: 14)-repB portion (base Nos. 3983 to 4676 of SEQ ID NO: 14) and containing no MembB, MobA, OriFI, and oriT regions.

Moreover, examples of the fragment of a plasmid of *Escherichia coli* used in the present invention can include plasmid fragments containing an *Escherichia coli* replication origin (ori) region (base Nos. 6356 to 6999 of SEQ ID NO: 14) and containing no ampicillin resistance gene (ampR) or lacking DNA encoding a β-lactamase region which is an expression product of the ampicillin resistance gene (ampR).

The promoter and the terminator of a gene encoding the HU protein derived from a bacterium of the genus *Bifidobacterium*, which are used in the step (2) of the construction method of the present invention, can be obtained by an approach known in the art. More specifically, based on the sequence of an HU protein of a bacterium of the genus *Bifidobacterium* known in the art, a gene encoding the HU protein of a bacterium of the genus *Bifidobacterium* can be cloned to thereby obtain a promoter and a terminator of the gene.

For example, sequences containing the promoter and the terminator of a gene encoding the HU protein derived from *Bifidobacterium longum* can be preferably exemplified by DNA as set forth in base Nos. 234 to 1481 of SEQ ID NO: 14 or 15 and DNA as set forth in base Nos. 2979 to 3098 of SEQ ID NO: 14 (base Nos. 3021 to 3140 of SEQ ID NO: 15), respectively.

The anaerobic microorganism transformed with the expression vector according to the present invention for constructing the anaerobic microorganism as the gene delivery carrier of the present invention is not particularly limited as long as it can be used in the present invention. It is preferred that the anaerobic microorganism should be an anaerobic bacterium, more preferably an enteric bacterium, even more preferably a bacterium of the genus *Bifidobacterium*.

Examples of the bacterium of the genus *Bifidobacterium* include *Bifidobacterium adolescentis*, *Bifidobacterium animalis*, *Bifidobacterium infantis*, *Bifidobacterium thermophilum*, *Bifidobacterium pseudolongum*, *Bifidobacterium bifidum*, *Bifidobacterium breve*, and *Bifidobacterium longum*. The *Bifidobacterium longum* is most preferred.

All of these bacteria are commercially available or can be obtained easily from depository institutions. For example, *Bifidobacterium longum* ATCC-15707, *Bifidobacterium bifidum* ATCC-11863, and *Bifidobacterium infantis* ATCC-15697 can be obtained easily from ATCC (The American Type Culture Collection).

Moreover, strains of each bacterium are not particularly limited. Examples of *Bifidobacterium longum* strains can include *Bifidobacterium longum* 105-A, *Bifidobacterium longum* aE-194b, *Bifidobacterium longum* bs-601, and *Bifidobacterium longum* M101-2 strains. Among them, the *Bifidobacterium longum* 105-A strain is preferable.

Examples of *Bifidobacterium breve* strains can include a *Bifidobacterium breve* type strain (JCM1192) and *Bifidobacterium breve* aS-1 and *Bifidobacterium breve* I-53-8W strains. Among them, the *Bifidobacterium breve* type strain and the *Bifidobacterium breve* aS-1 and *Bifidobacterium breve* I-53-8W strains are preferred.

Examples of *Bifidobacterium infantis* strains can include a *Bifidobacterium infantis* type strain (JCM1222) and a *Bifidobacterium infantis* I-10-5 strain. Among them, the *Bifidobacterium infantis* type strain and the *Bifidobacterium infantis* I-10-5 strain are preferred. Moreover, examples of *Bifidobacterium lactentis* strains can include a *Bifidobacterium lactentis* type strain (JCM1220).

Examples of the protein having an antitumor activity according to the present invention include cytokines.

Examples of specific cytokines include interferon (IFN)-α, β, or γ, granulocyte-macrophage colony-stimulating factor (GM-CSF), interleukin (IL)-1α, 1β, 2, 3, 4, 6, 7, 10, 12, 13, 15, or 18, tumor necrosis factor (TNF)-α, lymphotoxin (LT)-β, granulocyte colony-stimulating factor (G-CSF), macrophage colony-stimulating factor (M-CSF), macrophage migration inhibitory factor (MIF), leukemia inhibitory factor (LIF), costimulatory factors B7 (CD80) and B7-2 (CD86) for T-cell activation, kit-ligand, and oncostatin M. Further examples thereof include angiogenesis inhibitors such as endostatin, angiostatin, and kringle-1, 2, 3, 4, or 5.

The sequences of these proteins are known for various organisms. Based on the sequence information, DNA encoding the protein having an antitumor activity, which is used in the present invention, can be obtained by an approach known in the art such as a PCR method.

Moreover, examples of the protein having an activity of converting an antitumor substance precursor to an antitumor substance according to the present invention can include CD which is an enzyme that converts 5-FC to an antitumor-active substance 5-FU.

In the gene delivery carrier of the present invention, the DNA incorporated in the step (3) may be any one of (a) a DNA encoding a protein having an antitumor activity and (b) a DNA encoding a protein having an activity of converting an antitumor substance precursor to an antitumor substance. However, (b) the DNA encoding a protein having an activity of converting an antitumor substance precursor to an antitumor substance is preferred. Particularly, DNA encoding CD which is an enzyme that converts an antitumor substance precursor 5-FC to an antitumor substance 5-FU is preferred.

For example, DNA isolated from plasmid pAdex1CSCD (Riken Gene Bank RDB No. 1591) containing DNA encoding CD derived from *Escherichia coli* or from plasmid pMK116 also containing DNA encoding CD derived from *Escherichia coli* can be used as such DNA encoding CD (D. A. Mead et al., Protein Engineering 1: 67-74 (1986)).

The DNA encoding CD derived from *Escherichia coli* corresponds to, for example, a nucleotide sequence from the 1494th to 2774th nucleotides in SEQ ID NO: 14 (nucleotide sequence from the 1536th to 2816th nucleotides in SEQ ID NO: 15). Moreover, its amino acid sequence corresponds to the amino acid sequence of SEQ ID NO: 28 except for initiation methionine.

The origin from which the CD according to the present invention is derived is not particularly limited. DNA which has, for example, 90% or higher, more preferably 95% or higher homology to the amino acid sequence of SEQ ID NO: 28 and encodes an amino acid sequence having a CD activity can also be used.

The method of constructing a gene delivery carrier according to the present invention may not comprise a step (5) of mutating (a) the DNA encoding a protein having an antitumor activity or (b) the DNA encoding a protein having an activity of converting an antitumor substance precursor to an antitumor substance. From the viewpoint of obtaining a more excellent antitumor activity or activity of converting an antitumor substance precursor to an antitumor substance, it is preferred that the method of constructing a gene delivery carrier according to the present invention further comprises the step (5) before the step (4).

Specifically, for example, after mutating the DNA encoding the gene of interest, the mutated DNA may be incorporated to an expression vector in the step (3). Alternatively, after preparing an expression vector in the step (3), the DNA portion encoding the gene of interest may be mutated. The step of mutating, after preparing an expression vector in the step (3), the DNA portion encoding the gene of interest is more specifically a step (5') of mutating (a) the DNA encoding a protein having an antitumor activity or (b) the DNA encoding a protein having an activity of converting an antitumor substance precursor to an antitumor substance, which has been incorporated to the expression vector prepared in the step (3).

Mutating means is not particularly limited, and an approach known in the art such as site-specific mutagenesis using PCR can be used.

A preferable site to be mutated differs depending on the protein of interest. When the protein of interest is *Escherichia coli* CD, it is preferred that aspartic acid encoded by a nucleotide sequence from the 2433rd to 2435th nucleotides in SEQ ID NO: 14 (nucleotide sequence from the 2475th to 2477th nucleotides in SEQ ID NO: 15) is substituted by another amino acid. It is more preferred that the aspartic acid encoded by a nucleotide sequence from the 2433rd to 2435th nucleotides in SEQ ID NO: 14 (nucleotide sequence from the 2475th to 2477th nucleotides in SEQ ID NO: 15) is substituted by alanine. The aspartic acid encoded by a nucleotide sequence from the 2433rd to 2435th nucleotides in SEQ ID NO: 14 (nucleotide sequence from the 2475th to 2477th nucleotides in SEQ ID NO: 15) corresponds to aspartic acid at the 315th position in the amino acid sequence of SEQ ID NO: 28.

This substitution produces a much more excellent CD activity than that produced in the absence of substitution.

Examples of the expression vector according to the present invention can include a CD expression vector for a bacterium of the genus *Bifidobacterium* in which DNA encoding CD has been incorporated. Specific examples thereof can include: a recombinant plasmid pBLES100-S-eCD carrying *Escherichia coli* coda inserted downstream of a *Bifidobacterium longum* hup promoter (see Patent Document 4 and Non-Patent Document 3); pAV001-HU-eCD (pAV001-HU9aa-eCD) modified from this pBLES100-S-eCD, which is capable of transforming *Bifidobacterium longum* or *Bifidobacterium breve*; and mutants of these plasmids.

In this context, the mutants of the plasmids mean vectors in which the DNA, for example, CD-encoding DNA, incorporated in the plasmids has been mutated, which are plasmids that can be used in the same manner as or more preferably than the unmutated original vectors. For example, a mutant of pBLES100-S-eCD means a mutant of plasmid DNA derived from pBLES100-S-eCD, which is a plasmid that can be used in the same manner as or more preferably than pBLES100-S-eCD in the present invention. Alternatively, a mutant of pAV001-HU-eCD means a mutant of plasmid DNA derived from pAV001-HU-eCD, which is a plasmid that can be used in the same manner as or more preferably than pAV001-HU-eCD in the present invention.

Such mutants of the plasmids can be preferably exemplified by a plasmid pAV001-HU-eCD-M968 (SEQ ID NO: 27) which is a plasmid in which a single-nucleotide mutation has been introduced in a CD coding region of the plasmid pAV001-HU-eCD. In the plasmid pAV001-HU-eCD-M968, aspartic acid as the amino acid corresponding to the 315th position in the amino acid sequence shown in SEQ ID NO: 28 has been substituted by alanine. As a result, a CD activity is remarkably improved.

The gene delivery carrier of the present invention is not particularly limited as long as it is a gene delivery carrier consisting of an anaerobic microorganism transformed with an expression vector having a fragment of a plasmid of a bacterium of the genus *Bifidobacterium*, a fragment of a plasmid of *Escherichia coli*, and a DNA fragment comprising a promoter and a terminator of a gene encoding a histone-like DNA-binding protein derived from a bacterium of the genus *Bifidobacterium*, having, between the promoter and the terminator, (a) a DNA encoding a protein having an antitumor activity or (b) a DNA encoding a protein having an activity of converting an antitumor substance precursor to an antitumor substance, and further comprising a DNA fragment comprising a nucleotide sequence encoding a peptide consisting of an amino acid sequence from the 1st to at least 4th amino acids at the N-terminus of the histone-like DNA-binding protein, on the 5'-terminal side of (a) the DNA encoding a protein having an antitumor activity or (b) the DNA encoding a protein having an activity of converting an antitumor substance precursor to an antitumor substance.

The gene delivery carrier of the present invention can be constructed by, for example, the method of constructing a gene delivery carrier according to the present invention.

In the gene delivery carrier of the present invention, when the DNA encoding the protein of interest is unmutated, the DNA encoding a peptide consisting of an amino acid sequence at the N-terminus of the HU protein, which is comprised on the 5'-terminal side of the DNA encoding the protein, may not include DNA encoding a peptide consisting of an amino acid sequence from the 1st to 9th amino acids at the N-terminus of the HU protein.

Moreover, (a) the DNA encoding a protein having an antitumor activity or (b) the DNA encoding a protein having an activity of converting an antitumor substance precursor to an antitumor substance in the gene delivery carrier of the present invention may be an unmutated DNA. However, it is preferred that (a) the DNA encoding a protein having an antitumor activity or (b) the DNA encoding a protein having an activity of converting an antitumor substance precursor to an antitumor substance is mutated DNA such that the antitumor activity of a protein encoded by the mutated DNA or the activity thereof of converting an antitumor precursor to an antitumor substance is improved, compared with that of a protein encoded by DNA before mutation.

Examples of the gene delivery carrier of the present invention obtained using an expression vector having the mutated DNA encoding the protein of interest can include a single-nucleotide mutant plasmid of *Bifidobacterium longum* 105-A/pAV001-HU-eCD. Particularly, it can be preferably exemplified by *Bifidobacterium longum* 105-A/pAV001-HU-eCD-M968.

A method of constructing the gene delivery carrier of the present invention comprises the step of transforming an anaerobic microorganism with the expression vector in which the DNA encoding the protein of interest has been incorporated.

The construction of the transformed microorganism can be performed according to a method described in commercially available experimental manuals, for example, Gene Manual (Kodansha Ltd.), Method for Experiments in Gene Manipulation ed. by Yasutaka Takagi (Kodansha Ltd.), Molecular Cloning, Cold Spring Harbor Laboratory (1982), Molecular Cloning, 2nd ed., Cold Spring Harbor Laboratory (1989), or Methods in Enzymol., 194 (1991).

When the protein (b) having an activity of converting an antitumor substance precursor to an antitumor substance in the gene delivery carrier of the present invention is CD, it is required for application to enzyme-prodrug therapies that the CD-expressing genetically modified microorganism has a resistance to 5-FU at a concentration at least effective for an antitumor activity, which is converted from 5-FC by CD. However, when a 5-FU-resistant bacterium was constructed by an acclimation culture method described in Example 1 in Patent Document 5 using the CD-expressing genetically modified microorganism, a plasmid retention rate tended to decrease. However, in the method of constructing a gene delivery carrier according to the present invention, a 5-FU-resistant bacterium having a resistance to 5-FU at a concentration at least effective for an antitumor activity is first constructed as an anaerobic microorganism used as a host by an acclimation culture method described in Example 2 in Patent Document 5. This bacterium can be used as a host to thereby construct a genetically modified microorganism having a high plasmid retention rate.

A pharmaceutical composition of the present invention is not particularly limited as long as it comprises the gene delivery carrier of the present invention. Moreover, a therapeutic agent for solid tumor of the present invention is not particularly limited as long as it comprises the gene delivery carrier of the present invention.

The pharmaceutical composition or the therapeutic agent for solid tumor of the present invention may comprise one kind or two or more kinds of the gene delivery carrier(s) of the present invention.

Moreover, the dose of the gene delivery carrier in the pharmaceutical composition or the therapeutic agent for solid tumor of the present invention is not particularly limited as long as it is an amount sufficient for its growth in a tumor site and for expression of a therapeutically effective amount of a protein having an antitumor activity or an amount sufficient for expression of a protein in an amount capable of converting an antitumor substance precursor to a therapeutically effective amount of an antitumor substance. From a economic viewpoint and the viewpoint of circumventing side effects as much as possible, it is preferred that the dose of the gene delivery carrier is as small as possible within a range that produces a necessary antitumor activity. Moreover, the dose of the gene delivery carrier in the pharmaceutical composition or the therapeutic agent for solid tumor of the present invention can be appropriately selected according to the severity of disease and the body weight, age, and sex of a patient and can also be appropriately increased or decreased according to the degree of improvement.

Furthermore, the pharmaceutical composition or the therapeutic agent for solid tumor of the present invention may contain arbitrary ingredients in addition to the gene delivery carrier of the present invention unless the effects of the present invention are impaired. Examples of such arbitrary ingredients include pharmacologically acceptable carriers, excipients, and diluents.

When the gene delivery carrier or the therapeutic agent for solid tumor of the present invention is an anaerobic bacterium incorporating therein a gene from which a protein having an activity of converting an antitumor substance precursor to an antitumor substance can be expressed, the pharmaceutical composition or the therapeutic agent for solid tumor of the present invention comprising the gene delivery carrier as an active ingredient can be used in combination with an antitumor substance precursor in an amount capable of being converted to an effective amount of an antitumor substance by a protein expressed by the gene delivery carrier. This antitumor substance precursor may be contained in the pharmaceutical composition or the therapeutic agent for solid tumor comprising the gene delivery carrier of the present invention as an active ingredient. However, it is preferred that the antitumor substance precursor should be used in the form of a pharmaceutical composition comprising the antitumor substance precursor, in combination with the pharmaceutical composition or the therapeutic agent for solid tumor comprising the gene delivery carrier of the present invention as an active ingredient.

The dose of the antitumor substance precursor can be appropriately selected according to the growth rate of the gene delivery carrier used in combination therewith in a tumor tissue, and the efficiency of conversion of the antitumor substance precursor to an antitumor substance. Moreover, similarly with the dose of the gene delivery carrier, the dose of the antitumor substance precursor can be appropriately selected according to the severity of disease and the body weight, age, and sex of a patient and can also be appropriately increased or decreased according to the degree of improvement.

Thus, when the pharmaceutical composition or the therapeutic agent for solid tumor of the present invention is used in combination with the antitumor substance precursor, a method of administering the pharmaceutical composition or the therapeutic agent for solid tumor of the present invention may be the same as or different from a method of administering the pharmaceutical composition comprising the antitumor substance precursor. Moreover, they may be administered simultaneously or at time intervals. It is preferred that the pharmaceutical composition comprising the antitumor substance precursor is administered after the administration of the pharmaceutical composition or the therapeutic agent for solid tumor of the present invention such that the gene delivery carrier of the present invention can sufficiently grow in a tumor cell.

The phrase "comprising X in combination with Y" in the present invention encompasses both of the case in which X and Y are in different forms and the case in which X and Y are in the same form (e.g., a form comprising both X and Y). Moreover, when X and Y are in different forms, both X and Y may further contain other ingredients.

The dosage form of the pharmaceutical composition or the therapeutic agent for solid tumor of the present invention is not particularly limited. Examples thereof can include a liquid or solid preparation comprising the gene delivery carrier of the present invention. The liquid preparation can be produced by: purifying a culture solution of the anaerobic bacterium as the gene delivery carrier of the present invention; if necessary, adding thereto an appropriate saline solution or fluid replacement or pharmaceutical additives; and filling the mixture to an ampoule or vial or the like. Further, the solid preparation can be produced by adding an appropriate protective agent to the liquid preparation, filling the mixture to an ampoule or vial or the like, and then freeze-drying or L-drying; or by adding an appropriate protective agent to the liquid preparation, freeze-drying or L-drying the mixture, and then filling to an ampoule or vial or the like. A method of administering the pharmaceutical composition or the therapeutic agent for solid tumor of the present invention is preferably parenteral administration. For example, hypodermic injection, intravenous injection, local injection, and intracerebroventricular administration can be performed. The intravenous injection is most preferred.

The pharmaceutical composition or the therapeutic agent for solid tumor of the present invention can be applied to tumors having an anaerobic environment, preferably, various solid tumors. Examples of the solid tumors include colon-rectum cancer, brain tumor, head and neck cancer, breast cancer, lung cancer, esophagus cancer, gastric cancer, liver cancer, gallbladder cancer, bile duct cancer, pancreatic cancer, pancreatic islet cell cancer, choriocarcinoma, colon cancer, renal cell cancer, adrenal cortex cancer, urinary bladder cancer, testis cancer, prostatic cancer, testicle tumor, ovarian cancer, uterine cancer, choriocarcinoma, thyroid cancer, malignant carcinoid tumor, skin cancer, malignant melanoma, osteosarcoma, soft tissue sarcoma, neuroblastoma, Wilms tumor, retinoblastoma, melanoma, and squamous cell carcinoma.

Hereinafter, the present invention will be described more specifically with reference to Examples. However, the technical scope of the present invention is not intended to be limited to these exemplifications.

Reference Example 1

Preparation of *Bifidobacterium longum* 105-A/pAV001-HU-eCD (1) Construction of Shuttle Plasmid pAV001
(Construction of Plasmid)

A sequence containing spectinomycin adenyltransferase (AAD cassette) derived from *Enterococcus faecalis* was amplified by PCR from a shuttle plasmid pBLES100 of *Bifidobacterium longum* and *Escherichia coli* (see Patent Document 4 and Non-Patent Document 7), and the PCR product was subcloned into a PCR-BluntII-TOPO vector (Invitrogen Corp.) to prepare PCRTOPO-ScaI-AAD-Eam1105I. ScaI and Eam1105I restriction sites were added to forward and reverse primers, respectively.

As shown in FIG. 1, a cloning vector pGFPuv (DEFINITION: Cloning vector pGFPuv. ACCESSION: U62636; VERSION: U62636.1 GI: 1490528) purchased from Invitrogen Corp. is composed of a GFPuv gene, Multi-Cloning sites (MCSs) at both ends thereof, an ampicillin resistance gene, and an *Escherichia coli* plasmid replication origin.

The ampicillin resistance gene site in this pGFPuv was removed by cleavage with restriction enzymes Eam1105I and ScaI to prepare a long fragment. Similarly, PCRTOPO-ScaI-AAD-Eam1105I was cleaved with restriction enzymes Eam1105I and ScaI to prepare a fragment (approximately 1100 bp) containing the AAD cassette. These two fragments were ligated using T4 DNA ligase to prepare pGFPuv-SpR. The addition of a spectinomycin resistance trait and a loss of the ampicillin resistance trait in the prepared plasmid pGFPuv-SpR were respectively confirmed in *Escherichia coli*.

pGFPuv-SpR was digested with restriction enzymes SalI (located in the multi-cloning site upstream of the GFPuv gene) and SpeI (located in the multi-cloning site downstream of the GFPuv gene) to prepare a plasmid pAVN from which the GFPuv gene had been deleted.

Next, from information about the full-length nucleotide sequence of a plasmid pTB6 derived from *Bifidobacterium longum*, an approximately 1900-bp sequence containing RepB, SDO, DDO, AT-rich repeats, and DnaA-binding motifs was identified as a plasmid replication unit of *Bifidobacterium longum*. The approximately 1900-bp sequence containing the plasmid replication unit of *Bifidobacterium longum* was amplified by PCR from pTB6, and the PCR product was subcloned into a PCR-BluntII-TOPO vector to prepare PCRTOPO-ApaI-1900-ScaI. ApaI and ScaI restriction sites were added to forward and reverse primers, respectively.

The long fragment (approximately 2400 bp) obtained by digesting pAVN with restriction enzymes ApaI and ScaI and a short fragment (approximately 1900 bp) obtained by digesting PCRTOPO-ApaI-1900-ScaI with restriction enzymes ApaI and ScaI in the same way were ligated using T4 DNA ligase to prepare a *Bifidobacterium longum-Escherichia coli* shuttle plasmid pAV001 (approximately 4300 bp).

(2) CD Gene Expression Vector pAV001-HU-eCD
(Construction of Expression Vector)

Next, pBLES100-S-eCD was cleaved with restriction enzymes HindIII and SpeI to extract an approximately 2900-bp fragment containing an HU gene promoter, an *Escherichia coli*-derived CD gene, and an HU gene terminator. Similarly, the shuttle plasmid pAV001 was cleaved with HindIII and SpeI at the restriction sites in the multi-cloning sites. The obtained long fragment and the approximately 2900-bp fragment described above were ligated using T4 DNA ligase to prepare pAV001-HU-eCD (approximately 7100 bp).

(3) Introduction of CD Gene Expression Vector pAV001-HU-eCD into Bacterium of Genus *Bifidobacterium*

Wild-type *Bifidobacterium longum* was cultured in an MRS medium at 37° C. under anaerobic conditions, and the bacterial cells were separated from the culture solution by centrifugation and suspended in an appropriate buffer solution to prepare a bacterial suspension. Next, the CD gene expression vector pAV001-HU-eCD was introduced into the bacterial suspension using an electroporation method described in Non-Patent Documents 2 and 3. The introduced recombinant *Bifidobacterium longum* (*Bifidobacterium longum*/pAV001-HU-eCD) was selected based on colony formation on an agar medium containing an antibiotic spectinomycin.

(4) Cytosine Deaminase Enzyme Activity in *Bifidobacterium longum*/pAV001-HU-eCD; Measurement of 5-FC-5-FU Conversion Activity

Figure 2:
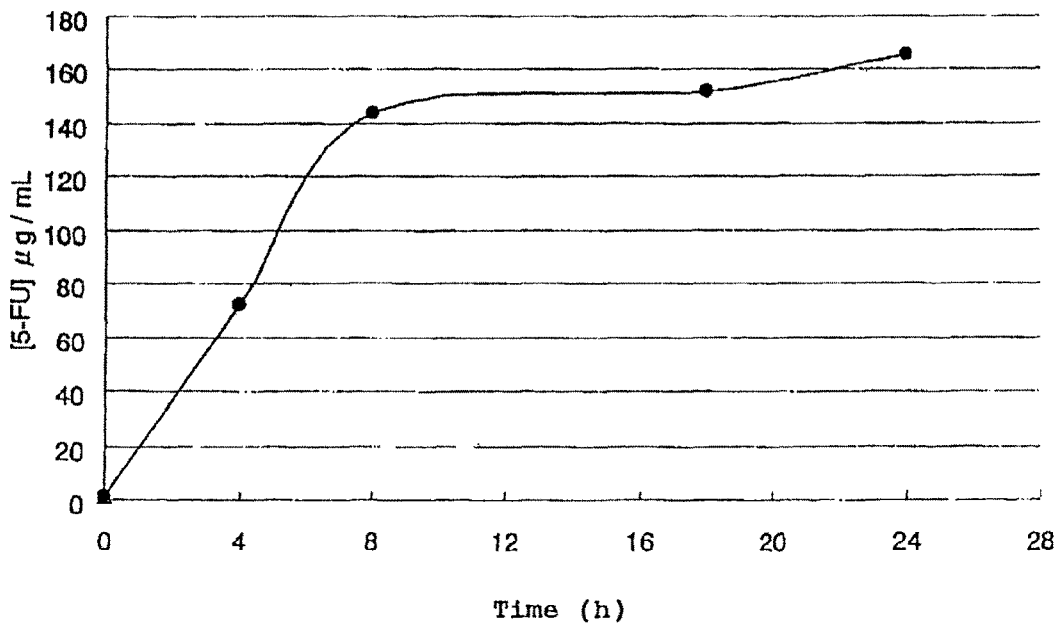
FIG. 2
It is a diagram showing a CD activity (concentration of 5-FU converted from 5-FC) in *Bifidobacterium longum* 105A/pAV001-HU-eCD.

*Bifidobacterium longum*/pAV001-HU-eCD was subcultured in an MRS medium containing an antibiotic spectinomycin at 37° C. for 2 days or longer under anaerobic conditions, and the bacterial cells ($2 \times 10^9$ CFU) were separated from the culture solution by centrifugation and suspended again in 4.5 mL of an MRS medium. Next, 0.5 mL of 5-FC (20 mg/mL) was added thereto, resulting in a final concentration of 2 mg/mL, and the bacterial cells were cultured at 37° C. under anaerobic conditions. After 0, 4, 8, 18, and 24 hours, supernatants of the culture solutions from which the bacterial cells had been removed by centrifugation were respectively collected. Converted 5-FU concentrations were measured by gas chromatography analysis (5-FU GC-MS methods, BML). The measurement results are shown in FIG. 2. As a result of analysis, in *Bifidobacterium longum*/pAV001-HU-eCD, 5-FU was detected at a concentration of 72.5 µg/mL after 4 hours and at a concentration of 165.4 µg/mL after 24 hours.

Example 1

Preparation of HU-eCD Plasmid

Figure 3:
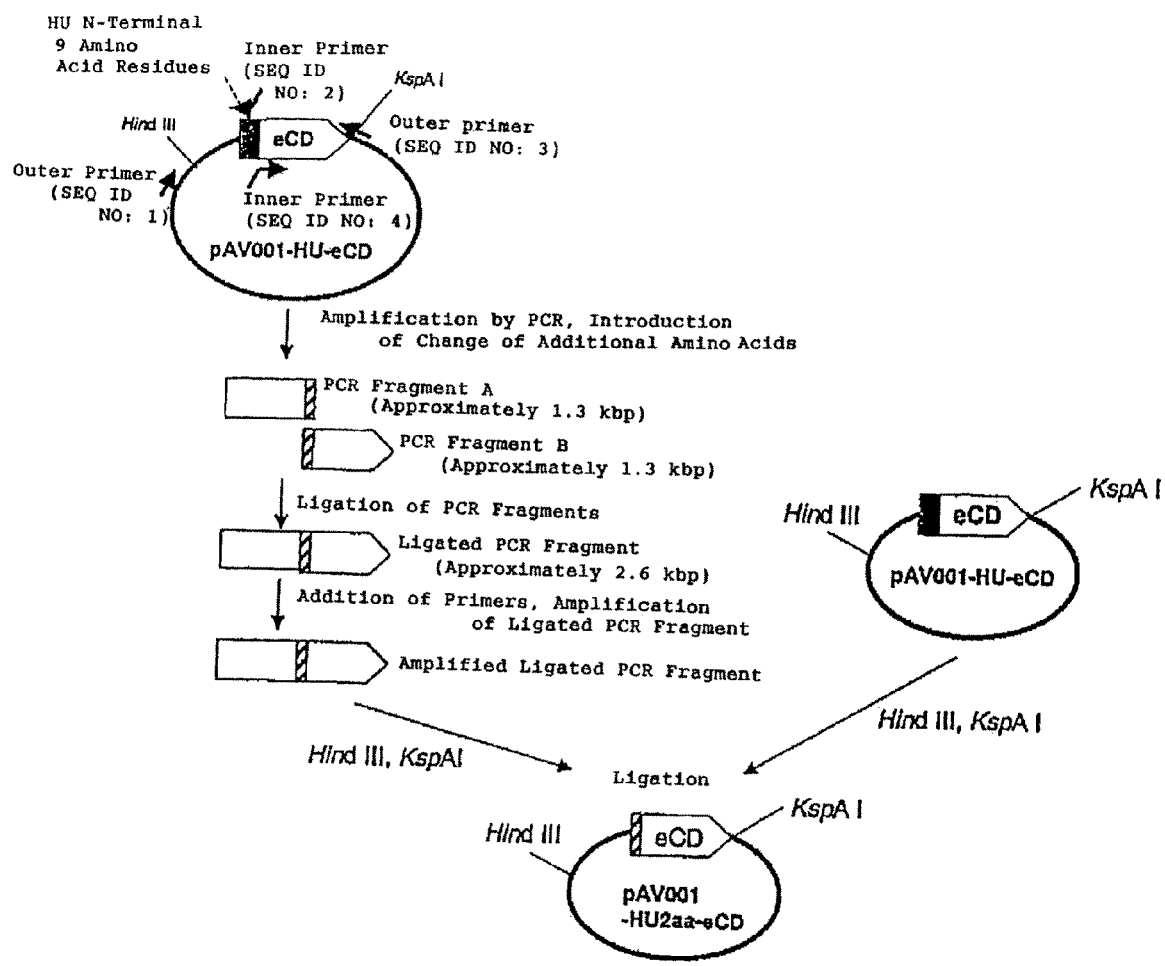
FIG. 3
It is a diagram showing the process of constructing an HU protein N-terminal 2-amino acid-adding plasmid.

Plasmids were constructed such that the length of the N-terminal region of an HU protein fused to the N-terminal region of eCD was changed to 2 amino acids, 3 amino acids, or 4 amino acids (FIG. 3).

Plasmids from which the sequence encoding the N-terminus of an HU protein was deleted were constructed in the same way. In this case, two kinds of plasmids were prepared, one with a translation start codon ATG of *Escherichia coli* JM101 strain-derived CD, and the other with a translation start codon GTG of *Escherichia coli* K12 strain-derived CD. Moreover, a plasmid was also constructed such that the length of the N-terminal region of an HU protein fused to the N-terminal region of eCD was changed to 18 amino acids. The sequences of the constructed portions of the plasmids are shown in Table 1.

TABLE 1

Plasmid construction table

| Plasmid name | Sequence proximal to CD N-terminus |
|---|---|
| pAV001-HU0aaATG | ATG TCG AAT AAC ... <br> M   S   N   N |
| pAV001-HU0aaGTG | GTG TCG AAT AAC ... <br> M   S   N   N |
| pAV001-HU2aa-eCD | ATG GCA TCG AAT AAC ... <br> M   A   S   N   N |
| pAV001-HU3aa-eCD | ATG GCA TAC TCG AAT AAC ... <br> M   A   Y   S   N   N |
| pAV001-HU4aa-eCD | ATG GCA TAC AAC TCG AAT AAC ... <br> M   A   Y   N   S   N   N |
| pAV001-HU-eCD (Control, pAV001-HU9aa-eCD) | ATG GCA TAC AAC AAG TCT GAG CTC GTT TCG AAT AAC ... <br> M   A   Y   N   K   S   D   L   V   S   N   N |
| pAV001-HU18aa-eCD | ATG GCA TAC AAC AAG TCT GAC CTC GTT TCG AAG ATC GCC <br> M   A   Y   N   K   S   D   L   V   S   K   I   A <br> CAG AAG TCC AAC CTG TCG AAT AAC ... <br> Q   K   S   N   L   S   N   N |

The term in bold type represents a sequence added to the CD N-terminus.

(1) Construction of HU Protein N-Terminal 2-Amino Acid-Adding Plasmid

PCR amplification was performed using 50 pg of pAV001-HU-eCD as a template and PrimeSTAR™ HS DNA Polymerase (Takara Bio Inc.) to obtain PCR fragments A (approximately 1.3 kbp) and B (approximately 1.3 kbp). An outer primer as set forth in SEQ ID NO: 1 and an inner primer as set forth in SEQ ID NO: 2 that had, at the 5'-terminus, a sequence overlapping with the terminus of the PCR fragment B and contained a sequence complementary to pAV001-HU-eCD were used in the amplification of the PCR fragment A.

The PCR fragment A contains, a HindIII site derived from the template at the terminus of DNA. An outer primer as set forth in SEQ ID NO: 3 that had, a KspAI recognition site on the 5'-terminal side and contained a sequence complementary to pAV001-HU-eCD and an inner primer as set forth in SEQ ID NO: 4 that had a sequence overlapping with the terminus of the PCR fragment A on the 5'-terminal side and contained a sequence complementary to pAV001-HU-eCD were used in the amplification of the PCR fragment B.

The change of the amino acid sequence derived from the HU protein was performed by inner primers. Temperature conditions involved 30 cycles each involving 98° C. for 10 seconds, 55° C. for 5 seconds, and 72° C. for 80 seconds, followed by incubation at 72° C. for 30 seconds. The PCR fragments A and B were purified using QIAquick PCR Purification Kit (QIAGEN), and the purified PCR fragments A and B were then mixed at equal moles.

Reaction at 5 cycles each involving 98° C. for 10 seconds and 72° C. for 90 seconds was performed in the absence of primers in a mixture solution of 1× PrimeSTAR™ buffer, 200 µM dNTPs mix, and 2.5 u PrimeSTAR™ HS DNA polymerase using 1 ng of the mixture of the purified PCR fragments A and B as a template to ligate the PCR fragments A and B. Then, the outer primers (SEQ ID NOs: 1 and 3) were added thereto, resulting in each final concentration of 0.5 µM, and reaction at 25 cycles each involving 98° C. for 10 seconds, 55° C. for 5 seconds, and 72° C. for 160 seconds was performed, followed by incubation at 72° C. for 30 seconds to obtain a ligated PCR product (approximately 2.6 kbp).

The ligated PCR product was separated on a 1% Sea-Plaque® GTG® Agarose gel (1×TAE buffer, 0.5 µg/ml ethidium bromide) to excise a 2.6-kbp DNA fragment. The ligated PCR product was extracted from the gel using QIAquick® Gel Extraction Kit and digested with HindIII (Fermentas UAB) and KspAI (Fermentas UAB). A 2.6-kbp DNA band was excised by separation on a 1% SeaPlaque® GTG® Agarose gel (1×TAE buffer, 0.5 µg/ml ethidium bromide). The ligated PCR product was extracted from the gel using QIAquick® Gel Extraction Kit.

The pAV001-HU-eCD vector was digested with HindIII (Fermentas UAB) and KspAI (Fermentas UAB). Then, a 4.6-kbp DNA fragment was excised by separation on a 1% SeaPlaque® GTG® Agarose gel (1×TAE buffer, 0.5 µg/ml ethidium bromide). Subsequently, the vector DNA was extracted from the gel using QIAquick® Gel Extraction Kit.

The ligated PCR product was mixed with the vector at a vector-to-ligated PCR product ratio of 1:3 by mol, and ligation was performed using Rapid DNA Ligation Kit (Fermentas UAB). *Escherichia coli* JM109 was transformed with the ligation product, and the strains were plated onto an LB agar medium containing 30 µg/ml spectinomycin and cultured overnight at 37° C. to obtain transformants. The transformants were cultured overnight at 37° C. in a 2×LB liquid medium containing 30 µg/ml spectinomycin, and plasmid DNA (pAV001-HU2aa-eCD) was extracted using QIAprep® Spin Miniprep Kit.

(2) Construction of HU Protein N-Terminal 3-Amino Acid-Adding Plasmid

An HU protein N-terminal 3-amino acid-adding plasmid (pAV001-HU3aa-eCD) was constructed in the same way as in the construction of the HU protein N-terminal 2-amino acid-adding plasmid except that primers as set forth in SEQ ID NOs: 5 and 4 were used as inner primers for amplification of PCR fragments A and B, respectively.

(3) Construction of HU Protein N-Terminal 4-Amino Acid-Adding Plasmid

An HU protein N-terminal 4-amino acid-adding plasmid (pAV001-HU4aa-eCD) was constructed in the same way as in the construction of the HU protein N-terminal 2-amino acid-adding plasmid except that primers as set forth in SEQ ID NOs: 6 and 7 were used as inner primers for amplification of PCR fragments A and B, respectively. The sequence of pAV001-HU4aa-eCD is shown in SEQ ID NO: 14.

(4) Construction of Plasmid Lacking Sequence Encoding N-Terminus of HU Protein and Having Translation Start Codon ATG A plasmid lacking the N-terminus of an HU protein and having the translation start codon ATG (pAV001-HU0aaATG-eCD) was constructed in the same way as in the construction of the HU protein N-terminal 2-amino acid-adding plasmid except that primers as set forth in SEQ ID NOs: 8 and 9 were used as inner primers for amplification of PCR fragments A and B, respectively.

(5) Construction of Plasmid the N-Terminus of HU Protein and Having Translation Start Codon GTG A plasmid lacking the N-terminus of an HU protein and having the translation start codon GTG (pAV001-HU0aaGTG-eCD) was constructed in the same way as in the construction of the HU protein N-terminal 2-amino acid-adding plasmid except that primers as set forth in SEQ ID NOs: 10 and 11 were used as inner primers for amplification of PCR fragments A and B, respectively.

(6) Construction of HU Protein N-Terminal 18-Amino Acid-Adding Plasmid

Two kinds of 5'-terminally phosphorylated synthetic oligo-DNAs (SEQ ID NOs: 12 and 13) having sequences complementary to each other were mixed at equal moles and annealed by decreasing temperatures in stages to 65° C. for 5 minutes, 45° C. for 5 minutes, 37° C. for 10 minutes, and 25° C. for 10 minutes in the presence of 0.1 M NaCl to prepare an adapter. The terminus of the adapter is a Bsp119I site.

The pAV001-HU-eCD vector was digested with Bsp119I (Fermentas UAB). After dephosphorylation treatment of the DNA terminus using CIAP (Fermentas UAB), the resulting DNA fragment was ligated with the adaptor using Rapid DNA Ligation Kit (Fermentas UAB). *Escherichia coli* JM109 strains were transformed with the ligation product, and the strains were plated onto an LB agar medium containing 30 µg/ml spectinomycin and cultured overnight at 37° C. to obtain transformants. The transformants were cultured overnight at 37° C. in a 2×LB liquid medium containing 30 µg/ml spectinomycin, and plasmid DNA (pAV001-HU18aa-eCD) was extracted using QIAprep® Spin Miniprep Kit. The sequence of pAV001-HU18aa-eCD is shown in SEQ ID NO: 15.

(Transformation of *Bifidobacterium longum* 105A)

80 µl of *Bifidobacterium longum* 105A competent cells and 5 µl (500 to 1000 ng) of the plasmid DNA were mixed, and transformation was performed using a Gene Pulser II electroporation system (Bio-Rad Laboratories, Inc., Japan). The strains were plated onto an IWATA agar medium containing 15% D-raffinose and 30 µg/ml spectinomycin and then cultured at 37° C. for two nights under anaerobic conditions to obtain transformants.

(Protein Extraction from *Bifidobacterium longum* 105A Transformants)

The transformants were inoculated into 5 ml of an MRS liquid medium (containing 30 µl/ml spectinomycin and a cysteine-vitamin C mixture solution) and cultured overnight at 37° C. under anaerobic conditions. 1% of the culture solution was inoculated into a medium having the same composition and cultured overnight at 37° C. under anaerobic conditions. This step was repeated twice. Protein extraction was performed using 1% of the culture solution inoculated in a medium having the same composition and cultured for approximately 18 hours. 4 ml of a Tris buffer solution (0.5 M Tris-HCl, 0.5% Triton X-100, pH 8.4) was added to 1 to 4 ml of the culture solution and mixed, followed by centrifugation at 13,000×g at room temperature for 15 minutes to remove the supernatant. The bacterial cells were suspended by the addition of 5 ml of a Tris buffer solution having the same composition, followed by centrifugation at 13,000×g at room temperature for 15 minutes to remove the supernatant. This procedure was repeated twice to wash the bacterial cells. The washed bacterial cells were suspended in 1 ml of a Tris buffer solution supplemented with 50 µl of a protease inhibitor (Sigma-Aldrich) and ultrasonically disrupted for 5 minutes under ice-cooling. After centrifugation at 13,000×g at 4° C. for 20 minutes, the supernatant was subjected to CD activity measurement as a total protein extract.

(CD Activity Measurement)

The amount of the total protein was measured by a modification of the Lowry method. A buffer solution was added to the total protein extract corresponding to an amount of the total protein of 50 µl to prepare 250 µl of a solution, which was then mixed with 250 µl of 40 mM 5-FC and then reacted at 60° C. for 20 minutes. The reaction was terminated by the addition of 250 µl of 0.5 M trichloroacetic acid, and the reaction product was left on ice. After centrifugation at 20,000×g at 4° C. for 20 minutes, 150 µl of 0.3 M NaOH was added to 450 µl of the supernatant to neutralize the solution.

The neutralized sample was diluted 10 folds with an HPLC mobile layer, and the amounts of 5-FU and 5-FC were measured by HPLC. Consumption % of 5-FC was used as a CD activity. The activity measurement results are shown in Table 2.

TABLE 2

Effect of adding amino acids derived from HU protein N-terminus to CD

| Transformant name | CD activity 5-FC consumption (%)/50 µg of total protein |
|---|---|
| *B. longum* 105A/pAV001-HU0aaATG | 1.89 |
| *B. longum* 105A/pAV001-HU0aaGTG | 1.08 |
| *B. longum* 105A/pAV001-HU2aa-eCD | 0.64 |
| *B. longum* 105A/pAV001-HU3aa-eCD | 2.80 |
| *B. longum* 105A/pAV001-HU4aa-eCD | 6.35 |
| *B. longum* 105A/pAV001-HU-eCD (Control) | 5.50 |
| *B. longum* 105A/pAV001-HU18aa-eCD | 6.48 |

It was demonstrated that the addition of amino acids derived from the HU protein N-terminus to eCD enhances a CD activity. With respect to the number of amino acids added, 2 or less amino acids were ineffective; 3 amino acids produced somewhat effects; and 4 or more amino acids produced dramatically increased effects. No difference in activity was observed between 4 and 18 amino acids.

Example 2

Preparation of *Bifidobacterium longum* 105-A/pAV001-HU-eCD Plasmid Mutant

A mutation was introduced to 5 sites in the plasmid pAV001-HU-eCD.

There were 2 types of mutations introduced: a 3-nucleotide deletion and a 1-nucleotide substitution. The deletion-type mutant plasmids were pAV001-HU-eCD-D37 and pAV001-HU-eCD-D55, and the nucleotide substitution-type mutant plasmids were pAV001-HU-eCD-M450, pAV001-HU-eCD-M968, and pAV001-HU-eCD-M1277. Methods of constructing the mutant plasmids are shown below.

(1) Construction of Mutant Plasmid (pAV001-HU-eCD-D37)

PCR amplification was performed using 50 pg of pAV001-HU-eCD as a template and PrimeSTAR™ HS DNA Polymerase (Takara Bio Inc.) to obtain PCR fragments A (approximately 1.3 kbp) and B (approximately 1.3 kbp). An outer primer as set forth in SEQ ID NO: 1 and an inner primer as set forth in SEQ ID NO: 16 that had a sequence overlapping with the terminus of the PCR fragment B on the 5'-terminal side, and contained a sequence complementary to pAV001-HU-eCD were used in the amplification of the PCR fragment A. The PCR fragment A contains, at the terminus of DNA, a HindIII site derived from the template. An outer primer as set forth in SEQ ID NO: 3 that had, a KspAI recognition site on the 5'-terminal side and contained a sequence complementary to pAV001-HU-eCD and an inner primer as set forth in SEQ ID NO: 17 that had, on the 5'-terminal side, a sequence overlapping with the terminus of the PCR fragment A and contained a sequence complementary to pAV001-HU-eCD were used in the amplification of the PCR fragment B. The mutation was introduced into the plasmid by inner primers. Temperature conditions involved 30 cycles each involving 98° C. for 10 seconds, 55° C. for 5 seconds, and 72° C. for 80 seconds, followed by incubation at 72° C. for 30 seconds. The PCR fragments A and B were purified using QIAquick PCR Purification Kit (QIAGEN), and the purified PCR fragments A and B were then mixed at equal moles. Reaction at 5 cycles each involving 98° C. for 10 seconds and 72° C. for 90 seconds was performed in the absence of primers in a mixture solution of 1× PrimeSTAR™ buffer, 200 μM dNTPs mix, and 2.5 u PrimeSTAR™ HS DNA polymerase using 1 ng of the mixture of the purified PCR fragments A and B as a template to ligate the PCR fragments A and B. Then, the outer primers (SEQ ID NOs: 1 and 3) were added thereto, resulting in each final concentration of 0.5 μM, and reaction at 25 cycles each involving 98° C. for 10 seconds, 55° C. for 5 seconds, and 72° C. for 160 seconds was performed, followed by incubation at 72° C. for 30 seconds to obtain a ligated PCR product (approximately 2.6 kbp). The ligated PCR product was separated on a 1% SeaPlaque® GTG® Agarose gel (1×TAE buffer, 0.5 μg/ml ethidium bromide) to excise a 2.6-kbp DNA band. The ligated PCR product was extracted from the gel using QIAquick® Gel Extraction Kit and digested with HindIII (Fermentas UAB) and KspAI (Fermentas UAB). A 2.6-kbp DNA band was excised by separation on a 1% SeaPlaque® GTG® Agarose gel (1×TAE buffer, 0.5 μg/ml ethidium bromide). The ligated PCR product was extracted from the gel using QIAquick® Gel Extraction Kit.

The pAV001-HU-eCD vector was digested with HindIII (Fermentas UAB) and KspAI (Fermentas UAB). Then, a 4.6-kbp DNA fragment was excised by separation on a 1% SeaPlaque® GTG® Agarose gel (1×TAE buffer, 0.5 μg/ml ethidium bromide). The vector DNA was extracted from the gel using QIAquick® Gel Extraction Kit. The ligated PCR product was mixed with the vector at a vector-to-ligated PCR product ratio of 1:3 by mol, and ligation was performed using Rapid DNA Ligation Kit (Fermentas UAB). *Escherichia coli* JM109 was transformed with the ligation product, and the strains were plated onto an LB agar medium containing 30 μg/ml spectinomycin and then cultured overnight at 37° C. to obtain transformants. The transformants were cultured overnight at 37° C. in a 2×LB liquid medium containing 30 μg/ml spectinomycin, and plasmid DNA (pAV001-HU-eCD-D37) was extracted using QIAprep® Spin Miniprep Kit.

The pAV001-HU-eCD-D37 is a plasmid having a CD gene lacking a nucleotide sequence (nucleotide sequence encoding alanine at the 5th position in SEQ ID NO: 28) from the 1503rd to 1505th nucleotides in SEQ ID NO: 14 (1545th to 1547th nucleotides in SEQ ID NO: 15).

(2) Construction of Mutant Plasmid (pAV001-HU-eCD-D55)

pAV001-HU-eCD-D55 was constructed in the same way as in the construction of the plasmid pAV001-HU-eCD-D37 except that primers as set forth in SEQ ID NOs: 18 and 19 were used as inner primers for amplification of PCR fragments A and B, respectively.

The pAV001-HU-eCD-D55 is a plasmid having a CD gene lacking a nucleotide sequence (nucleotide sequence encoding asparagine at the 11th position in SEQ ID NO: 28) from the 1521st to 1523rd nucleotides in SEQ ID NO: 14 (1563rd to 1565th nucleotides in SEQ ID NO: 15).

(3) Construction of Mutant Plasmid (pAV001-HU-eCD-M450)

pAV001-HU-eCD-M450 was constructed in the same way as in the construction of the plasmid pAV001-HU-eCD-D37 except that primers as set forth in SEQ ID NOs: 20 and 21 were used as inner primers for amplification of PCR fragments A and B, respectively, and except for PCR reaction conditions.

With respect to the PCR reaction conditions, reaction temperature conditions for amplification of the PCR fragment A involved 30 cycles each involving 98° C. for 10 seconds, 55° C. for 5 seconds, and 72° C. for 105 seconds, followed by incubation at 72° C. for 30 seconds, and reaction temperature conditions for amplification of the PCR fragment B involved 30 cycles each involving 98° C. for 10 seconds, 55° C. for 5 seconds, and 72° C. for 1 minute, followed by incubation at 72° C. for 30 seconds. Moreover, for ligation of the PCR products, reaction at 5 cycles each involving reaction temperatures 98° C. for 10 seconds and 72° C. for 105 seconds was performed.

The pAV001-HU-eCD-M450 is a plasmid having a CD gene in which a nucleotide sequence (nucleotide sequence encoding glutamine at the 142nd position in SEQ ID NO: 28) from the 1914th to 1916th nucleotides in SEQ ID NO: 14 (1956th to 1958th nucleotides in SEQ ID NO: 15) has been substituted by a nucleotide sequence encoding histidine.

(4) Construction of Mutant Plasmid (pAV001-HU-eCD-M968)

pAV001-HU-eCD-M968 was constructed in the same way as in the construction of the plasmid pAV001-HU-eCD-D37 except that primers as set forth in SEQ ID NOs: 22 and 23 were used as inner primers for amplification of PCR fragments A and B, respectively, and a primer as set forth in SEQ ID NO: 24 was used as an outer primer for amplification of the PCR fragment B, and except for PCR reaction conditions.

With respect to the PCR reaction conditions, reaction temperature conditions for amplification of the PCR fragment A involved 30 cycles each involving 98° C. for 10 seconds, 55° C. for 5 seconds, and 72° C. for 130 seconds, followed by incubation at 72° C. for 30 seconds, and reaction temperature conditions for amplification of the PCR fragment B involved 30 cycles each involving 98° C. for 10 seconds, 55° C. for 5 seconds, and 72° C. for 45 seconds, followed by incubation at 72° C. for 30 seconds. Moreover, for ligation of the PCR products, reaction at 5 cycles each involving reaction temperatures 98° C. for 10 seconds and 72° C. for 130 seconds was performed. For amplification of the ligated PCR product, reaction at 25 cycles each involving 98° C. for 10 seconds, 55°

C. for 5 seconds, and 72° C. for 3 minutes was performed using primers as set forth in SEQ ID NOs: 1 and 24, followed by incubation at 72° C. for 30 seconds to obtain a ligated PCR product (approximately 2.9 kbp). The pAV001-HU-eCD vector was digested with HindIII (Takara Bio Inc.) and SpeI (Takara Bio Inc.), and a fragment (approximately 4.3 kbp) excised from an agarose gel was used as a vector for the ligated PCR product. The sequence of the obtained pAV001-HU-eCD-M968 is shown in SEQ ID NO: 27.

The pAV001-HU-eCD-M968 is a plasmid having a CD gene in which a nucleotide sequence (nucleotide sequence encoding aspartic acid at the 315th position in SEQ ID NO: 28) from the 2433rd to 2435th nucleotides in SEQ ID NO: 14 (2475th to 2477th nucleotides in SEQ ID NO: 15) has been substituted by a nucleotide sequence encoding alanine.

(5) Construction of Mutant Plasmid (pAV001-HU-eCD-M1277)

pAV001-HU-eCD-M1277 was constructed in the same way as in the construction of the plasmid pAV001-HU-eCD-M968 except that primers as set forth in SEQ ID NOs: 25 and 26 were used as inner primers for amplification of PCR fragments A and B, respectively, and except for PCR reaction conditions.

With respect to the PCR reaction conditions, reaction temperature conditions for amplification of the PCR fragment A involved 30 cycles each involving 98° C. for 10 seconds, 55° C. for 5 seconds, and 72° C. for 150 seconds, followed by incubation at 72° C. for 30 seconds, and reaction temperature conditions for amplification of the PCR fragment B involved 30 cycles each involving 98° C. for 10 seconds, 55° C. for 5 seconds, and 72° C. for 30 seconds, followed by incubation at 72° C. for 30 seconds. Moreover, for ligation of the PCR products, reaction at 5 cycles each involving reaction temperatures 98° C. for 10 seconds and 72° C. for 150 seconds was performed.

The pAV001-HU-eCD-M1277 is a plasmid having a CD gene in which a nucleotide sequence (nucleotide sequence encoding glutamic acid at the 418th position in SEQ ID NO: 28) from the 2742nd to 2744th nucleotides in SEQ ID NO: 14 (2784th to 2786th nucleotides in SEQ ID NO: 15) has been substituted by a nucleotide sequence encoding glycine.

(Transformation of *Bifidobacterium longum* 105A)

*Bifidobacterium longum* 105A was transformed with the obtained mutant plasmid in the same way as in Example 1 to obtain its transformants.

(Protein Extraction from *Bifidobacterium longum* 105A Transformants)

A protein extract was obtained from the *Bifidobacterium longum* 105A transformed with the mutant plasmid, in the same way as in Example 1, and the protein extract was subjected to CD activity measurement.

(CD Activity Measurement)

A CD activity was measured in the same way as in Example 1 using the obtained protein extract. The activity measurement results are shown in Table 3.

TABLE 3

Change in CD activity brought by introduction of mutation into pAV001-HU-eCD

| Transformant name | CD activity 5-FC consumption (%)/50 μg of total protein |
| --- | --- |
| *B. longum* 105A/pAV001-HU-eCD-M450 | 4.13 |
| *B. longum* 105A/pAV001-HU-eCD-M968 | 65.8 |
| *B. longum* 105A/pAV001-HU-eCD-M1277 | 5.30 |

TABLE 3-continued

Change in CD activity brought by introduction of mutation into pAV001-HU-eCD

| Transformant name | CD activity 5-FC consumption (%)/50 μg of total protein |
| --- | --- |
| *B. longum* 105A/pAV001-HU-eCD (Control) | 5.50 |

*Bifidobacterium longum* 105A/pAV001-HU-eCD-M968 obtained by transformation with the mutant pAV001-HU-eCD-M968 has a CD activity improved to approximately 12 times that of *Bifidobacterium longum* 105A/pAV001-HU-eCD (control) obtained by transformation with unmutated pAV001-HU-eCD.

On the other hand, *Bifidobacterium longum* 105A/pAV001-HU-eCD-M450 and *Bifidobacterium longum* 105A/pAV001-HU-eCD-M1277 obtained by transformation with the mutants pAV001-HU-eCD-M450 and pAV001-HU-eCD-M1277, respectively, were not confirmed to have a rise in activity due to the introduction of the mutation.

Example 3

Preparation of 5-FU-Resistant *Bifidobacterium longum* 105A/pAV001-HU-eCD Plasmid Mutant (Addition of 5-FU Resistance to *Bifidobacterium longum* 105A/pAV001-HU-eCD-M968)

The *Bifidobacterium longum* 105A/pAV001-HU-eCD-M968 obtained in Example 2 was made into a 5-FU-resistant mutant according to the method described in Example 1 in Patent Document 5.

Specifically, the *Bifidobacterium longum* 105A/pAV001-HU-eCD-M968 obtained in Example 2 was subcultured in an MRS medium at 37° C. for 2 days or longer under anaerobic conditions. The culture solution was diluted with an anaerobic diluent and then plated onto a BL agar medium containing 500 μg/mL 5-FU, and the bacteria were anaerobically cultured at 37° C. for 2 or 3 days. Then, the grown bacteria were selected to prepare 5-FU-resistant *Bifidobacterium longum* 105A/pAV001-HU-eCD-M968 (*Bifidobacterium longum* 105A-R1/pAV001-HU-eCD-M968).

(Transformation of 5-FU-Resistant *Bifidobacterium longum* 105A with Plasmid pAV001-HU-eCD-M968)

5-FU-resistant *Bifidobacterium longum* 105A prepared according to the method described in Example 2 in Patent Document 5 was transformed with the mutant plasmid pAV001-HU-eCD-M968 obtained in Example 2, in the same way as in Example 1, and transformants thereof were obtained.

Specifically, *Bifidobacterium longum* 105A was inoculated into 5 mL of an MRS medium containing 100 μg/mL 5-FU and anaerobically cultured at 37° C. for 1 to 5 days. The turbidity (OD=600 nm) thereof was measured to examine the presence or absence of the growth. 1 mL of the medium after culture in which the growth had been confirmed was recovered and inoculated into 9 mL of an MRS medium containing the same concentration of 5-FU, and the bacteria were cultured for 24 hours under the same culture conditions. This inoculation procedure was repeated three times to thereby prepare 5-FU-resistant *Bifidobacterium longum* 105A. Next, this 5-FU-resistant *Bifidobacterium longum* 105A was inoculated into an MRS medium. The bacterial solution after culture was inoculated into an MRS medium containing 250

μg/mL 5-FU. After 24 hours, the presence or absence of the growth was determined using turbidity (OD=600 nm). The 5-FU-resistant *Bifidobacterium longum* 105A prepared using a medium containing 100 μg/mL 5-FU (*Bifidobacterium longum* 105A-R2) was used as a host for transformation. This *Bifidobacterium longum* 105A-R2 was transformed with the mutant plasmid pAV001-HU-eCD-M968 obtained in Example 2, in the same way as in Example 1, and its transformant *Bifidobacterium longum* 105A-R2/pAV001-HU-eCD-M968 was prepared.

Example 4

Protein Extraction from *Bifidobacterium longum* 105A-R2/pAV001-HU-eCD-M968)

A protein extract was obtained from the *Bifidobacterium longum* 105A-R2/pAV001-HU-eCD-M968 thus obtained, in the same way as in Example 1, and the protein extract was subjected to CD activity measurement.
(CD Activity Measurement)
As a result of CD activity measurement in the same way as in Example 1 using the obtained protein extract, the *Bifidobacterium longum* 105A-R2/pAV001-HU-eCD-M968 also exhibited a CD activity equivalent to that of the transformed *Bifidobacterium longum* 105A of Example 2, as shown in Table 4.

TABLE 4

| Transformant name | CD activity 5-FC consumption (%)/50 μg of total protein |
|---|---|
| *Bifidobacterium longum* 105A/pAV001-HU-eCD-M968 | 65.8 |
| *Bifidobacterium longum* 105A-R2/pAV001-HU-eCD-M968 | 62.4 |

Example 5

Measurement of Plasmid Retention Stability

Figure 4:
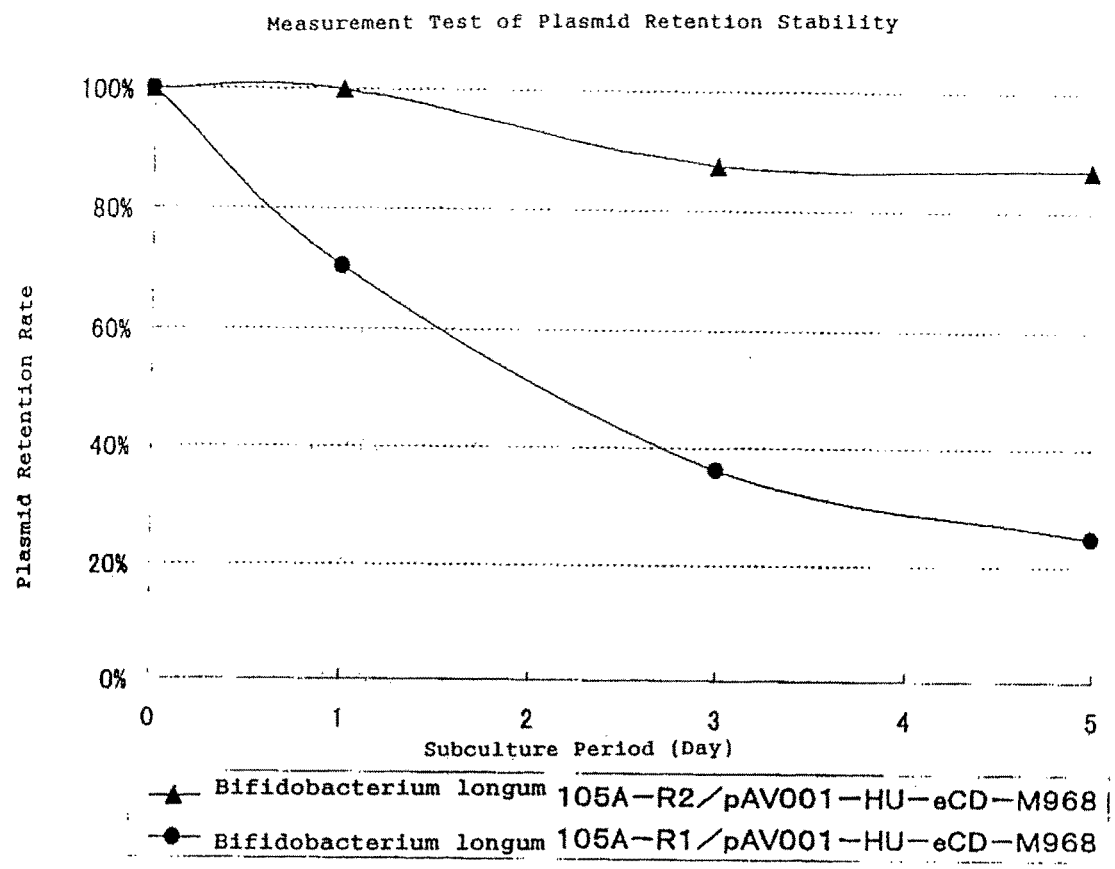
FIG. 4
It is a diagram showing results of plasmid retention rates of two kinds of 5-FU-resistant *Bifidobacterium longum* 105A/pAV001-HU-eCD-M968.

With respect to the *Bifidobacterium longum* 105A-R2/pAV001-HU-eCD-M968 (R2 strain) and the *Bifidobacterium longum* 105A-R1/pAV001-HU-eCD-M968 (R1 strain) obtained in Example 3, plasmid retention stability was measured by a method described below. As a result, the R2 strain exhibited much more favorable plasmid retention stability than that of the R1 strain, as shown in FIG. 4.

(Measurement Test of Plasmid Retention Stability)
The measurement of the plasmid retention stability was performed by the following test method: the R2 and R1 strains were separately cultured in a liquid medium supplemented with an antibiotic (spectinomycin) as a selective marker for the introduced plasmids, to sufficiently activate the transformed *Bifidobacterium longum* R2 and R1 strains. This bacterial solution was designated as a subculture day-0 bacterial solution. Next, an aliquot of the day-0 bacterial solution was recovered and inoculated into a spectinomycin-free liquid medium, followed by culture. This bacterial solution was designated as a subculture day-1 bacterial solution. Similarly, an aliquot of the day-1 bacterial solution was recovered and inoculated into a spectinomycin-free liquid medium, followed by culture to prepare a subculture day-2 bacterial solution. Subculture was continuously performed in the same way until day 5 to prepare up to day-3 to day-5 bacterial solutions. The day-0, day-1, day-3, and day-5 bacterial solutions were separately plated onto an antibiotic-free plate medium (BL agar medium) to form colonies. 100 grown colonies were randomly selected for each culture and inoculated into both spectinomycin-containing and spectinomycin-free BL agar media by a replica method using a sterilized toothpick or the like. Plasmid retention rates on day 0, day 1, day 3, and day 5 were measured from a numerical formula described below. The results are shown in FIG. 4.

The plasmid retention rates were calculated from the following formula:

$$\text{Plasmid retention rate (\%)} = \frac{\text{The number of colonies in spectinomycin-containing } BL \text{ agar medium}}{\text{The number of colonies in } BL \text{ agar medium}} \times 100$$

INDUSTRIAL APPLICABILITY

According to the present invention, a gene delivery carrier consisting of an anaerobic microorganism capable of growing in a tumor tissue in an anaerobic environment and capable of expressing a protein having an antitumor activity or a protein having an activity of converting an antitumor substance precursor to an antitumor substance, which is useful as a therapeutic agent for solid tumor and has a favorable activity and expression efficiency of a protein expressed by a gene introduced by transformation, can be constructed efficiency.

The invention claimed is:

1. A method of constructing a gene delivery carrier consisting of a bacterium of the genus *Bifidobacterium* transformed with an expression vector, comprising the steps of:
   (1) preparing a fusion plasmid having a fragment of a plasmid of a bacterium of the genus *Bifidobacterium* and a fragment of a plasmid of *Escherichia coli*;
   (2) incorporating a DNA fragment comprising a promoter and a terminator of the gene encoding the histone-like DNA-binding protein derived from a bacterium of the genus *Bifidobacterium* into the fusion plasmid;
   (3) incorporating, between the promoter and the terminator, a DNA encoding cytosine deaminase to obtain the expression vector, wherein the DNA comprises:
      (a) a DNA sequence encoding an amino acid sequence which: (i) deletes methionine at position 1; and (ii) replaces aspartic acid at position 315 with alanine from the amino acid sequence set forth in SEQ ID NO:28; and
      (b) a DNA sequence which encodes an amino acid sequence corresponding to positions 1 through at least 4 and up to a maximum of 18 amino acids of the histone-like DNA binding protein as set forth in SEQ ID NO: 29 and which is linked to (a) on the 5'-terminal side of (a); and
   (4) transforming the bacterium of the genus *Bifidobacterium* with the expression vector.

2. The method according to claim 1, wherein the bacterium of the genus *Bifidobacterium* is selected from *Bifidobacterium adolescentis*, *Bifidobacterium animalis*, *Bifidobacterium infantis*, *Bifidobacterium thermophilum*, *Bifidobacterium pseudolongum*, *Bifidobacterium bifidum*, *Bifidobacterium breve*, and *Bifidobacterium longum*.

3. The method according to claim 2, wherein the bacterium of the genus *Bifidobacterium* is *Bifidobacterium longum*.

4. The method according to claim 1, wherein the expression vector is a plasmid pAV001-HU-eCD-M968.

5. A gene delivery carrier consisting of a bacterium of the genus *Bifidobacterium* transformed with an expression vector comprising:
   (i) a fragment of a plasmid of a bacterium of the genus *Bifidobacterium*;
   (ii) a fragment of a plasmid of *Escherichia coli*;
   (iii) a DNA fragment comprising a promoter and a terminator of the gene encoding the histone-like DNA-binding protein derived from a bacterium of the genus *Bifidobacterium*; and
   (iv) a DNA encoding cytosine deaminase positioned between the promoter and the terminator, wherein the DNA comprises:
      (a) a DNA sequence encoding an amino acid sequence which: (1) deletes methionine at position 1; and (2) replaces aspartic acid at position 315 with alanine from the amino acid sequence set forth in SEQ ID NO: 28; and
      (b) a DNA sequence which encodes an amino acid sequence corresponding to positions 1 through at least 4 and up to a maximum of 18 amino acids of the histone-like DNA-binding protein as set forth in SEQ ID NO: 29 and which is linked to (a) on the 5'-terminal side of (a).

6. The gene delivery carrier according to claim 5, wherein the bacterium of the genus *Bifidobacterium* is any bacterium of the genus *Bifidobacterium* selected from *Bifidobacterium adolescentis*, *Bifidobacterium animalis*, *Bifidobacterium infantis*, *Bifidobacterium thermophilum*, *Bifidobacterium pseudolongum*, *Bifidobacterium bifidum*, *Bifidobacterium breve*, and *Bifidobacterium longum*.

7. The gene delivery carrier according to claim 6, wherein the bacterium of the genus *Bifidobacterium* is *Bifidobacterium longum*.

8. The gene delivery carrier according to claim 5, wherein the gene delivery carrier is capable of growing in a tumor tissue in an anaerobic environment.

9. The gene delivery carrier according to claim 8, wherein the gene delivery carrier is a cytosine deaminase-expressing 5-fluorouracil-resistant bacterium having a resistance to 5-fluorouracil at a concentration at least effective for an antitumor activity.

10. The gene delivery carrier according to claim 9, wherein the gene delivery carrier is a single-nucleotide mutant plasmid of *Bifidobacterium longum* 105-A/pAV001-HU-eCD, and wherein the single-nucleotide mutant plasmid of *Bifidobacterium longum* 105-A/pAV001-HU-eCD is *Bifidobacterium longum* 105-A/pAV001-HU-eCD-M968.

11. A pharmaceutical composition comprising a gene delivery carrier according to claim 5.

12. A pharmaceutical composition comprising a gene delivery carrier according to claim 8 in combination with 5-fluorocytosine converted to 5-fluorouracil by cytosine deaminase capable of being expressed by the gene delivery carrier.

13. A therapeutic agent for solid tumor comprising a gene delivery carrier according to claim 8 in an amount sufficient for expression of a cytosine deaminase in an amount capable of converting 5-fluorocytosine to a therapeutically effective amount of 5-fluorouracil, in combination with 5-fluorocytosine converted by the cytosine deaminase capable of being expressed by the gene delivery carrier, in an amount capable of being converted to a therapeutically effective amount of 5-fluorouracil.

14. A cytosine deaminase-highly-expressing unit comprising a DNA fragment comprising:
  (i) a promoter and a terminator of the gene encoding the histone-like DNA-binding protein derived from a bacterium of the genus *Bifidobacterium*; and
  (ii) a DNA encoding cytosine deaminase positioned between the promoter and the terminator, wherein the DNA comprises:
    (a) a DNA sequence encoding an amino acid sequence which: (1) deletes methionine at position 1; and (2) replaces aspartic acid at position 315 with alanine from the amino acid sequence set forth in SEQ ID NO: 28, and
    (b) a DNA sequence which encodes an amino acid sequence corresponding to positions 1 through at least 4 and up to a maximum of 18 amino acids of the histone-like DNA-binding protein as set forth in SEQ ID NO: 29 and which is linked to (a) on the 5'-terminal side of (a).

15. A cytosine deaminase-highly-expressing unit comprising a DNA fragment comprising:
  (i) a promoter and a terminator of the gene encoding the histone-like DNA-binding protein derived from a bacterium of the genus *Bifidobacterium*; and
  (ii) a DNA encoding cytosine deaminase positioned between the promoter and the terminator, wherein the DNA comprises:
    (a) a DNA sequence encoding an amino acid sequence which: (1) deletes methionine at position 1; and (2) replaces aspartic acid at position 315 with alanine from the amino acid sequence set forth in SEQ ID NO: 28, and
    (b) a DNA sequence which encodes the amino acid sequence corresponding to positions 1 through 9 of the histone-like DNA-binding protein as set forth in SEQ ID NO: 29 and which is linked to (a) on the 5'-terminal side of (a).

* * * * *

SEQUENCE LISTING

<160> NUMBER OF SEQ ID NOS: 29

<210> SEQ ID NO 1
<211> LENGTH: 23
<212> TYPE: DNA
<213> ORGANISM: Artificial Sequence
<220> FEATURE:
<223> OTHER INFORMATION: primer

<400> SEQUENCE: 1
tcacacagga aacagctatg acc                                          23

<210> SEQ ID NO 2
<211> LENGTH: 55

<210> SEQ ID NO 2
<211> LENGTH: 55
<212> TYPE: DNA
<213> ORGANISM: Artificial Sequence
<220> FEATURE:
<223> OTHER INFORMATION: primer

<400> SEQUENCE: 2
ggcgttaata attgtttgta aagcgttatt cgatgccata aagcatcctt cttgg    55

<210> SEQ ID NO 3
<211> LENGTH: 29
<212> TYPE: DNA
<213> ORGANISM: Artificial Sequence
<220> FEATURE:
<223> OTHER INFORMATION: primer

<400> SEQUENCE: 3
gaacacatcc tggaaggcgt taactcaac    29

<210> SEQ ID NO 4
<211> LENGTH: 43
<212> TYPE: DNA
<213> ORGANISM: Artificial Sequence
<220> FEATURE:
<223> OTHER INFORMATION: primer

<400> SEQUENCE: 4
tcgaataacg ctttacaaac aattattaac gcccggttac cag    43

<210> SEQ ID NO 5
<211> LENGTH: 58
<212> TYPE: DNA
<213> ORGANISM: Artificial Sequence
<220> FEATURE:
<223> OTHER INFORMATION: primer

<400> SEQUENCE: 5
ggcgttaata attgtttgta aagcgttatt cgagtatgcc ataaagcatc cttcttgg    58

<210> SEQ ID NO 6
<211> LENGTH: 54
<212> TYPE: DNA
<213> ORGANISM: Artificial Sequence
<220> FEATURE:
<223> OTHER INFORMATION: primer

<400> SEQUENCE: 6
ggcgttaata attgtttgta aagcgttatt cgagttgtat gccataaagc atcc    54

<210> SEQ ID NO 7
<211> LENGTH: 47
<212> TYPE: DNA
<213> ORGANISM: Artificial Sequence
<220> FEATURE:
<223> OTHER INFORMATION: primer

<400> SEQUENCE: 7
caactcgaat aacgctttac aaacaattat taacgcccgg ttaccag    47

<210> SEQ ID NO 8
<211> LENGTH: 58
<212> TYPE: DNA
<213> ORGANISM: Artificial Sequence
<220> FEATURE:
<223> OTHER INFORMATION: primer

<400> SEQUENCE: 8

```
gggcgttaat aattgtttgt aaagcgttat tcgacataaa gcatccttct tgggtcag    58

<210> SEQ ID NO 9
<211> LENGTH: 51
<212> TYPE: DNA
<213> ORGANISM: Artificial Sequence
<220> FEATURE:
<223> OTHER INFORMATION: primer

<400> SEQUENCE: 9
gctttatgtc gaataacgct ttacaaacaa ttattaacgc ccggttacca g    51

<210> SEQ ID NO 10
<211> LENGTH: 58
<212> TYPE: DNA
<213> ORGANISM: Artificial Sequence
<220> FEATURE:
<223> OTHER INFORMATION: primer

<400> SEQUENCE: 10
gggcgttaat aattgtttgt aaagcgttat tcgacacaaa gcatccttct tgggtcag    58

<210> SEQ ID NO 11
<211> LENGTH: 51
<212> TYPE: DNA
<213> ORGANISM: Artificial Sequence
<220> FEATURE:
<223> OTHER INFORMATION: primer

<400> SEQUENCE: 11
gctttgtgtc gaataacgct ttacaaacaa ttattaacgc ccggttacca g    51

<210> SEQ ID NO 12
<211> LENGTH: 27
<212> TYPE: DNA
<213> ORGANISM: Artificial Sequence
<220> FEATURE:
<223> OTHER INFORMATION: oligonucleotide

<400> SEQUENCE: 12
cgaagatcgc ccagaagtcc aacctgt    27

<210> SEQ ID NO 13
<211> LENGTH: 27
<212> TYPE: DNA
<213> ORGANISM: Artificial Sequence
<220> FEATURE:
<223> OTHER INFORMATION: oligonucleotide

<400> SEQUENCE: 13
cgacaggttg gacttctggg cgatctt    27

<210> SEQ ID NO 14
<211> LENGTH: 7148
<212> TYPE: DNA
<213> ORGANISM: Bifidobacterium longum

<400> SEQUENCE: 14
agcgcccaat acgcaaaccg cctctccccg cgcgttggcc gattcattaa tgcagctggc    60
acgacaggtt tcccgactgg aaagcgggca gtgagcgcaa cgcaattaat gtgagttagc    120
tcactcatta ggcaccccag gctttacact ttatgcttcc ggctcgtatg ttgtgtggaa    180
ttgtgagcgg ataacaattt cacacaggaa acagctatga ccatgattac gccaagcttg    240
gggagacacg acgttgacca cgttggcccc gttcattcag aaagtcgcgg tcccctcccc    300
```

```
cacacgcgca ttgggcacgt gggacaagca gctgctcaag gaactgcgag accacatcaa    360
caccataatc gatgaggaga ccgccgaatc cgccgagccg gtgacgctgg cccgcttctc    420
ttggcgttcg atgatcacca tgctgctggt catcgtggcc gtggtcgtgg tcttcaccca    480
actgaagccc gaggagatca tcaccgcgct gaccaacgcc aacccgttga tggcggtggt    540
gacgctcgcg ttcggtgtct gcggctggat cggctcgtcg atttcgctcg gttccctgat    600
ggcgcggcac aagcgtgaca atatgggcgt cttcatgagc caggtggcag gcggcttcgc    660
caccgtatcc atgccagccg gcgtgggccc ctcgttcgtc aacctgcagt tcctgcgcaa    720
atccggctat cgcaacaccc aggcgaccgc aattatgagc gccgcgctcg tggtgtatta    780
cgccgtgtac ttctccatgc tggtcatcat cggcctgttc accggccgca acatgttctc    840
cggcgcaatc ccgacaaaca cgttggttat cgtgctgggc gttgtggtcg tggtgctgtc    900
cattgcgatg atgattccgc cgttgcgcca ctgggtgacc cgtcgtctta tgccgctggc    960
caagacgtat atcaaccagc tgctggacgt gctttcccag ccccgacagc tcacagtcag   1020
ctgcctaggc gcgctgttcc agaacgcgac cactgggctc gctttctggg cggccctgca   1080
agcgttcggc tattcatcga atccgattga acgacgttc gtcttcctgc tggcctatgc   1140
attgggttcc gcagtgccca ctccaggcgg tctgggcggt gtggaagcgg cgctgacatt   1200
cgcgttcgtg gcggtcggag tgccgcaggg cgtggcgctt ccgccactt tgctgcaccg   1260 cgtggtgttc tactggctgc gcattccgct gggcgcggcg gccatgaagt ggcttgacaa   1320
gcataatctt gtctgattcg tctatttca taccccctc ggggaaatag atgtgaaaac   1380
ccttataaaa cgcgggtttt cgcagaaaca tgcgctagta tcattgatga caacatggac   1440
taagcaaaag tgcttgtccc ctgacccaag aaggatgctt tatggcatac aactcgaata   1500
acgctttaca aacaattatt aacgcccggt taccaggcga agaggggctg tggcagattc   1560
atctgcagga cggaaaaatc agcgccattg atgcgcaatc cggcgtgatg cccataactg   1620
aaaacagcct ggatgccgaa caaggtttag ttataccgcc gtttgtggag ccacatattc   1680
acctggacac cacgcaaacc gccggacaac cgaactggaa tcagtccggc acgctgtttg   1740
aaggcattga acgctgggcc gagcgcaaag cgttattaac ccatgacgat gtgaaacaac   1800
gcgcatggca aacgctgaaa tggcagattg ccaacggcat tcagcatgtg cgtacccatg   1860
tcgatgtttc ggatgcaacg ctaactgcgc tgaaagcaat gctggaagtg aagcaggaag   1920
tcgcgccgtg gattgatctg caaatcgtcg ccttccctca ggaagggatt ttgtcgtatc   1980
ccaacggtga agcgttgctg gaagaggcgt tacgcttagg ggcagatgta gtggggcga   2040 ttccgcattt tgaatttacc cgtgaatacg gcgtggagtc gctgcataaa accttcgccc   2100
tggcgcaaaa atacgaccgt ctcatcgacg ttcactgtga tgagatcgat gacgagcagt   2160
cgcgctttgt cgaaaccgtt gctgccctgg cgcaccatga aggcatgggc gcgcgagtca   2220
ccgccagcca caccacggca atgcactcct ataacgggc gtatacctca cgcctgttcc   2280
gcttgctgaa aatgtccggt attaactttg tcgccaaccc gctggtcaat attcatctgc   2340
aaggacgttt cgatacgtat ccaaaacgtc gcggcatcac gcgcgttaaa gagatgctgg   2400
agtccggcat taacgtctgc tttggtcacg atgatgtctt cgatccgtgg tatccgctgg   2460
gaacggcgaa tatgctgcaa gtgctgcata tggggctgca tgtttgccag ttgatgggct   2520
acgggcagat taacgatggc ctgaatttaa tcacccacca cagcgcaagg acgttgaatt   2580
tgcaggatta cggcattgcc gccggaaaca cgcgccaacct gattatcctg ccggctgaaa   2640
```

```
atgggtttga tgcgctgcgc cgtcaggttc cggtacgtta ttcggtacgt ggcggcaagg    2700
tgattgccag cacacaaccg gcacaaacca ccgtatatct ggagcagcca gaagccatcg    2760
attacaaacg ttgagttaac gccttccagg atgtgttcgt cgaggctatg aagtccggcg    2820
aaggcctgaa gctcaccggc ctgttctccg ctgagcgcgt caagcgcccg gctcgcaccg    2880
gccgcaaccc gcgcactggc gagcagattg acattccggc ttcctacggc gttcgtatct    2940
ccgctggctc cctgctgaag aaggccgtca ccgagtgacc ttctgctcgt agcgattact    3000
tcgagcatta ctgacgacaa agaccccgac cgagatggtc ggggtctttt tgttgtggtg    3060
ctgtgacgtg ttgtccaacc gtattattcc ggactagtcg gccgtacggg cccgataggc    3120
aggcccagct caaggcccgc gagaacgacc tcgtggcgcg cgcagggaa cgcgaacgca    3180
aggcccgcac caagcgcctg atcgaggtcg gcgcgatggc cgagtcggcc gcgggcttcg    3240
agggaggcga cgagagggcc aaggagcaca tcgcccgcct cgtgcagctc ggctccctgg    3300
tggagtccct gtgctccacc gacgtgatgg ccaactacac gagccgcgag gacctcaggg    3360
ccaccgtcgc caaggctctg gaacacaacg tcaggaccag cgatggcatg aactggaacc    3420
tccaggacct cgtctacgag gcgctgagcg aggaatggcg caaaagggac ggcgagatca    3480
gcgacccatg ggccaacgac gaggcggacg gataccagcc gccctcatac gagccggtca    3540
accccgaacg caggactccc cagacgcccc ccgatggcct gatctgacgt ccgaaaaaag    3600
gcgctgtgcg cccttttta atcttttata atcttttta cattctttta gccctccgc    3660
agccttactc tcccaacggg tttcagccga acctacacc aaaaggggag cgaacctaca    3720
ccaaaagggg agcgaaccta caccaaaagg ggagcgaacc tacaccaaaa ggggagctat    3780
atacacccttt tgttatttaa ggtgcaagtt gtgctatgct gaggccatgt ccatgagatc    3840
gtgaagttca gcaccagttc aacaacgtcg cgctgaagaa gttcgacgcc gtgcacctgg    3900
acgtgctcat ggcgatcgcc tcaagggtga gggagaaggg cacggccacg gtggagttct    3960
cgttcgagga gctgcgcggc ctcatgcgat tgaggaagaa cctgaccaac aagcagctgg    4020
ccgacaagat cgtgcagacg aacgcgcgcc tgctggcgct gaactacatg ttcgaggatt    4080
cgggcaagat catccagttc gcgctgttca cgaagttcgt caccgacccg caggaggcga    4140
ctctcgcggt tggggtcaac gaggagttcg cgttcctgct caacgacctg accagccagt    4200
tcacgcgctt cgagctggcc gagttcgccg acctcaagag caagtacgcc aaggagttct    4260
accgcagggc caagcagtac cgcagctccg gaatctggaa gatcggccgc gacgagttct    4320
gccgactgct tggcgttcca ccgtcggcaa taacccagac acgatatctg aatcagaagg    4380
ttcttcagcc aattcaggag gagtgtgggc ctctccttgg cctgaagatc gagcgccagt    4440
acgtgaaacg caggctgtcg ggcttcgtgt tcacattcgc ccgcgagacc cctccggtga    4500
tcgacgccag gcccgtggag gcgaggaaga cggacggcga cggcaagggc cattggacga    4560
gcgttgccgg gtacgcgag tgttcacga ccacggcgtt gttcgacgtg acggccgccc    4620
gggctcactt cgacggcacc gtggaggccg gggaatgccg tttctgcgcg tttgacgcgc    4680
gcaaccgcga acatcatgcg cggaacgccg aaggctgtt ctagcggccg tgtccgcgcc    4740
tctggggcgg ttgcgcctgc catgggtcga tctgccgctg ttcggcctca cgctggtctg    4800
tgcgctgcct gatctccctg agcaggtcgg ccttggtcct gggggcgctt cgctcctcga    4860
acgggccgct ctcccccagg tcctcgggct cgctcaggtc caacggctcg tcaccggacg    4920
gctcgggccg gttctctccc tgtgccgggt tctccgcctg tgcgcgttgt tcggccatgc    4980
gcagtgcgag ggccttcacc tgttcggggc ttagtacttg catgcctgca ggtcgatttt    5040
```

```
cgttcgtgaa tacatgttat aataactata actaataacg taacgtgact ggcaagagat    5100 attttaaaa caatgaatag gtttacactt actttagttt tatggaaatg aaagatcata    5160
tcatatataa tctagaataa aattaactaa aataattatt atctagataa aaaatttaga    5220
agccaatgaa atctataaat aaactaaatt aagtttattt aattaacaac tatggatata    5280
aaataggtac taatcaaaat agtgaggagg atatatttga atacatacga acaaattaat    5340
aaagtgaaaa aaatacttcg gagacattta aaaaataacc ttattggtac ttacatgttt    5400
ggatcaggag ttgagagtgg accaaaacca aatagtgatc ttgactttt agtcgtcgta     5460 tctgaaccat tgacagatca aagtaaagaa atacttatac aaaaaattag acctatttca    5520
aaaaaaatag gagataaaag caacttacga tatatcgaat taacgattat tattcagcaa    5580
gaaatggtac cgtggaatca tcctcccaaa caagaattta tttatggaga atggttacaa    5640
gagctttatg aacaaggata cattcctcag aaggaattaa attcagattt aaccataatg    5700
ctttaccaag caaaacgaaa aaataaaaga atatacggaa attatgactt agaggaatta    5760
ctacctgata ttccattttc tgatgtgaga agagccatta tggattcgtc agaggaatta    5820
atagataatt atcaggatga tgaaaccaac tctatattaa ctttatgccg tatgatttta    5880
actatggaca cgggtaaaat cataccaaaa gatattgcgg gaaatgcagt ggctgaatct    5940
tctccattag aacatgggga gagaattttg ttagcagttc gtagttatct tggagagaat    6000
attgaatgga ctaatgaaaa tgtaaattta actataaact atttaaataa cagattaaaa    6060
aaattataaa aaaattgaaa aaatggtgga aacactttt tcaattttt tgttttatta      6120 tttaatgggg accccgagtc aggcaactat ggatgaacga aatagacaga tcgctgagat    6180
aggtgcctca ctgattaagc attggtaact gtcagaccaa gtttactcat atatacttta    6240
gattgattta aaacttcatt tttaatttaa aaggatctag gtgaagatcc ttttgataa     6300 tctcatgacc aaaatccctt aacgtgagtt ttcgttccac tgagcgtcag accccgtaga    6360
aaagatcaaa ggatcttctt gagatccttt ttttctgcgc gtaatctgct gcttgcaaac    6420
aaaaaaacca ccgctaccag cggtggtttg tttgccggat caagagctac caactctttt    6480
tccgaaggta actggcttca gcagagcgca gataccaaat actgtccttc tagtgtagcc    6540
gtagttaggc caccacttca agaactctgt agcaccgcct acatacctcg ctctgctaat    6600
cctgttacca gtggctgctg ccagtggcga taagtcgtgt cttaccgggt tggactcaag    6660
acgatagtta ccggataagg cgcagcggtc gggctgaacg gggggttcgt gcacacagcc    6720
cagcttggag cgaacgacct acaccgaact gagatacgta cagcgtgagc tatgagaaag    6780
cgccacgctt cccgaaggga gaaaggcgga caggtatccg gtaagcggca gggtcggaac    6840
aggagagcgc acgagggagc ttccaggggg aaacgcctgg tatctttata gtcctgtcgg    6900
gtttcgccac ctctgacttg agcgtcgatt tttgtgatgc tcgtcagggg ggcggagcct    6960
atggaaaaac gccagcaacg cggccttttt acgttcctg gccttttgct ggccttttgc     7020
tcacatgttc tttcctgcgt tatccctga ttctgtggat aaccgtatta ccgcctttga     7080
gtgagctgat accgctcgcc gcagccgaac gaccgagcgc agcgagtcag tgagcgagga    7140
agcggaag                                                            7148
```

<210> SEQ ID NO 15
<211> LENGTH: 7190
<212> TYPE: DNA
<213> ORGANISM: Bifidobacterium longum

```
<400> SEQUENCE: 15
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
tcactcatta ggcaccccag gctttacact ttatgcttcc ggctcgtatg ttgtgtggaa     180
ttgtgagcgg ataacaattt cacacaggaa acagctatga ccatgattac gccaagcttg     240
gggagacacg acgttgacca cgttggcccc gttcattcag aaagtcgcgg tcccctcccc     300
cacacgcgca ttgggcacgt gggacaagca gctgctcaag gaactgcgag accacatcaa     360
caccataatc gatgaggaga ccgccgaatc cgccgagccg gtgacgctgg cccgcttctc     420
ttggcgttcg atgatcacca tgctgctggt catcgtggcc gtggtcgtgg tcttcaccca     480
actgaagccc gaggagatca tcaccgcgct gaccaacgcc aacccgttga tggcggtggt     540
gacgctcgcg ttcggtgtct gcggctggat cggctcgtcg atttcgctcg gttccctgat     600
ggcgcggcac aagcgtgaca atatgggcgt cttcatgagc caggtggcag gcggcttcgc     660
caccgtatcc atgccagccg gcgtgggccc ctcgttcgtc aacctgcagt tcctgcgcaa     720
atccggctat cgcaacaccc aggcgaccgc aattatgagc gccgcgctcg tggtgtatta     780
cgccgtgtac ttctccatgc tggtcatcat cggcctgttc accggccgca acatgttctc     840
cggcgcaatc ccgacaaaca cgttggttat cgtgctgggc gttgtggtcg tggtgctgtc     900
cattgcgatg atgattccgc cgttgcgcca ctgggtgacc cgtcgtctta tgccgctggc     960
caagacgtat atcaaccagc tgctggacgt gctttcccag ccccgacagc tcacagtcag    1020
ctgcctaggc gcgctgttcc agaacgcgac cactgggctc gctttctggg cggccctgca    1080
agcgttcggc tattcatcga atccgattga aacgacgttc gtcttcctgc tggcctatgc    1140
attgggttcc gcagtgccca ctccaggcgg tctgggcggt gtggaagcgg cgctgacatt    1200
cgcgttcgtg gcggtcggag tgccgcaggg cgtggcgctt ccgccacttt gctgcaccg    1260
cgtggtgttc tactggctgc gcattccgct gggcgcggcg gccatgaagt ggcttgacaa    1320
gcataatctt gtctgattcg tctattttca tacccccttc gggaaatag atgtgaaaac    1380
ccttataaaa cgcgggtttt cgcagaaaca tgcgctagta tcattgatga caacatggac    1440
taagcaaaag tgcttgtccc ctgacccaag aaggatgctt tatggcatac aacaagtctg    1500
acctcgtttc gaagatcgcc cagaagtcca acctgtcgaa taacgcttta caaacaatta    1560
ttaacgcccg gttaccaggc gaagaggggc tgtggcagat tcatctgcag gacggaaaaa    1620
tcagcgcct tgatgcgcaa tccggcgtga tgcccataac tgaaaacagc ctggatgccg    1680
aacaaggttt agttataccg ccgtttgtgg agccacatat tcacctggac accacgcaaa    1740
ccgccggaca accgaactgg aatcagtccg gcacgctgtt tgaaggcatt gaacgctggg    1800
ccgagcgcaa agcgttatta acccatgacg atgtgaaaca acgcgcatgg caaacgctga    1860
aatggcagat tgccaacggc attcagcatg tgcgtaccca tgtcgatgtt tcggatgcaa    1920
cgctaactgc gctgaaagca atgctggaag tgaagcagga agtcgcgccg tggattgatc    1980
tgcaaatcgt cgccttccct caggaaggga ttttgtcgta tcccaacggt gaagcgttgc    2040
tggaagaggc gttacgctta ggggcagatg tagtgggggc gattccgcat tttgaattta    2100
cccgtgaata cggcgtggag tcgctgcata aaaccttcgc cctggcgcaa aaatacgacc    2160
gtctcatcga cgttcactgt gatgagatcg atgacgagca gtcgcgcttt gtcgaaaccg    2220
ttgctgccct ggcgcaccat gaaggcatgg gcgcgcgagt caccgccagc cacaccacgg    2280
caatgcactc ctataacggg gcgtatacct cacgcctgtt ccgcttgctg aaaatgtccg    2340
```

-continued

```
gtattaactt tgtcgccaac ccgctggtca atattcatct gcaaggacgt tcgatacgt    2400 atccaaaacg tcgcggcatc acgcgcgtta aagagatgct ggagtccggc attaacgtct    2460
gctttggtca cgatgatgtc ttcgatccgt ggtatccgct gggaacggcg aatatgctgc    2520
aagtgctgca tatggggctg catgtttgcc agttgatggg ctacgggcag attaacgatg    2580
gcctgaattt aatcacccac cacagcgcaa ggacgttgaa tttgcaggat tacggcattg    2640
ccgccggaaa cagcgccaac ctgattatcc tgccggctga aaatgggttt gatgcgctgc    2700
gccgtcaggt tccggtacgt tattcggtac gtggcggcaa ggtgattgcc agcacacaac    2760
cggcacaaac caccgtatat ctggagcagc cagaagccat cgattacaaa cgttgagtta    2820
acgccttcca ggatgtgttc gtcgaggcta tgaagtccgg cgaaggcctg aagctcaccg    2880
gcctgttctc cgctgagcgc gtcaagcgcc cggctcgcac cggccgcaac ccgcgcactg    2940
gcgagcagat tgacattccg gcttcctacg gcgttcgtat ctccgctggc tccctgctga    3000
agaaggccgt caccgagtga ccttctgctc gtagcgatta cttcgagcat tactgacgac    3060
aaagaccccg accgagatgg tcggggtctt tttgttgtgg tgctgtgacg tgttgtccaa    3120
ccgtattatt ccggactagt cggccgtacg ggcccgatag gcaggcccag ctcaaggccc    3180
gcgagaacga cctcgtggcg cggcgcaggg aacgcgaacg caaggcccgc accaagcgcc    3240
tgatcgaggt cggcgcgatg gccgagtcgg ccgcgggctt cgagggaggc gacgagaggg    3300
ccaaggagca catcgcccgc ctcgtgcagc tcggctccct ggtggagtcc ctgtgctcca    3360
ccgacgtgat ggccaactac acgagccgcg aggacctcag ggccaccgtc gccaaggctc    3420
tggaacacaa cgtcaggacc agcgatggca tgaactggaa cctccaggac ctcgtctacg    3480
aggcgctgag cgaggaatgg cgcaaaaggg acggcgagat cagcgaccca tgggccaacg    3540
acgaggcgga cggataccag ccgccctcat acgagccggt caaccccgaa cgcaggactc    3600
cccagacgcc ctccgatggc ctgatctgac gtccgaaaaa aggcgctgtg cgcccttttt    3660 aaatcttta taaatcttt tacattcttt tagcccctcc gcagccttac tctcccaacg    3720
ggtttcagcc gaaacctaca ccaaaagggg agcgaaccta caccaaaagg ggagcgaacc    3780
tacaccaaaa ggggagcgaa cctacaccaa aaggggagct atatacacct tttgttattt    3840
aaggtgcaag ttgtgctatg ctgaggccat gtccatgaga tcgtgaagtt cagcaccagt    3900
tcaacaacgt cgcgctgaag aagttcgacg ccgtgcacct ggacgtgctc atggcgatcg    3960
cctcaagggt gagggagaag ggcacggcca cggtggagtt ctcgttcgag gagctgcgcg    4020
gcctcatgcg attgaggaag aacctgacca acaagcagct ggccgacaag atcgtgcaga    4080
cgaacgcgcg cctgctggcg ctgaactaca tgttcgagga tcgggcaag atcatccagt    4140 tcgcgctgtt cacgaagttc gtcaccgacc cgcaggagc gactctcgcg gttgggtca    4200 acgaggagtt cgcgttcctg ctcaacgacc tgaccagcca gttcacgcgc ttcgagctgg    4260
ccgagttcgc cgacctcaag agcaagtacg ccaaggagtt ctaccgcagg ccaagcagt    4320 accgcagctc cggaatctgg aagatcggcc gcgacgagtt ctgccgactg cttggcgttc    4380
caccgtcggc aataacccag acacgatatc tgaatcagaa ggttcttcag ccaattcagg    4440
aggagtgtgg gcctctcctt ggcctgaaga tcgagcgcca gtacgtgaaa cgcaggctgt    4500
cgggcttcgt gttcacattc gcccgcgaga cccctccggt gatcgacgcc aggcccgtgg    4560
aggcgaggaa gacggacggc gacggcaagg gccattggac gagcgttgcc gggtacggcg    4620
aggtgttcac gaccacggcg ttgttcgacg tgacggccgc ccgggctcac ttcgacggca    4680
```

```
ccgtggaggc cggggaatgc cgtttctgcg cgtttgacgc gcgcaaccgc gaacatcatg    4740
cgcggaacgc cggaaggctg ttctagcggc cgtgtccgcg cctctgggc ggttgcgcct     4800 gccatgggtc gatctgccgc tgttcggcct cacgctggtc tgtgcgctgc ctgatctccc    4860
tgagcaggtc ggccttggtc ctgggggcgc ttcgctcctc gaacgggccg ctctccccca    4920
ggtcctcggg ctcgctcagg tccaacggct cgtcaccgga cggctcgggc cggttctctc    4980
cctgtgccgg gttctccgcc tgtgcgcgtt gttcggccat gcgcagtgcg agggccttca    5040
cctgttcggg gcttagtact tgcatgcctg caggtcgatt ttcgttcgtg aatacatgtt    5100
ataataacta taactaataa cgtaacgtga ctggcaagag atattttaa aacaatgaat     5160 aggtttacac ttactttagt tttatggaaa tgaaagatca tatcatatat aatctagaat    5220
aaaattaact aaaataatta ttatctagat aaaaaattta gaagccaatg aaatctataa    5280
ataaactaaa ttaagtttat ttaattaaca actatggata taaaataggt actaatcaaa    5340
atagtgagga ggatatattt gaatacatac gaacaaatta ataaagtgaa aaaaatactt    5400
cggagacatt taaaaaataa ccttattggt acttacatgt ttggatcagg agttgagagt    5460
ggaccaaaac caaatagtga tcttgactt ttagtcgtcg tatctgaacc attgacagat     5520
caaagtaaag aaatacttat acaaaaaatt agacctattt caaaaaaaat aggagataaa    5580
agcaacttac gatatatcga attaacgatt attattcagc aagaaatggt accgtggaat    5640
catcctccca aacaagaatt tatttatgga gaatggttac aagagcttta tgaacaagga    5700
tacattcctc agaaggaatt aaattcagat ttaaccataa tgctttacca agcaaaacga    5760
aaaaataaaa gaatatacgg aaattatgac ttagaggaat tactacctga tattccattt    5820
tctgatgtga gaagagccat tatggattcg tcagaggaat taatagataa ttatcaggat    5880
gatgaaacca actctatatt aactttatgc cgtatgattt taactatgga cacgggtaaa    5940
atcataccaa agatattgc gggaaatgca gtggctgaat cttctccatt agaacatagg    6000
gagagaattt tgttagcagt tcgtagttat cttggagaga atattgaatg gactaatgaa    6060
aatgtaaatt taactataaa ctatttaaat aacagattaa aaaaattata aaaaaattga    6120
aaaaatggtg gaaacacttt tttcaatttt tttgttttat tatttaatgg ggaccccgag    6180
tcaggcaact atggatgaac gaaatagaca gatcgctgag ataggtgcct cactgattaa    6240
gcattggtaa ctgtcagacc aagtttactc atatatactt tagattgatt taaaacttca    6300
tttttaattt aaaaggatct aggtgaagat ccttttgat aatctcatga ccaaaatccc     6360
ttaacgtgag ttttcgttcc actgagcgtc agaccccgta gaaaagatca aaggatcttc    6420
ttgagatcct ttttttctgc gcgtaatctg ctgcttgcaa acaaaaaaac caccgctacc    6480
agcggtggtt tgtttgccgg atcaagagct accaactctt tttccgaagg taactggctt    6540
cagcagagcg cagataccaa atactgtcct tctagtgtag ccgtagttag gccaccactt    6600
caagaactct gtagcaccgc ctacatacct cgctctgcta atcctgttac cagtggctgc    6660
tgccagtggc gataagtcgt gtcttaccgg gttggactca agacgatagt taccggataa    6720
ggcgcagcgg tcgggctgaa cggggggttc gtgcacacag cccagcttgg agcgaacgac    6780
ctacaccgaa ctgagatacc tacagcgtga gctatgagaa agcgccacgc ttcccgaagg    6840
gagaaaggcg gacaggtatc cggtaagcgg cagggtcgga acaggagagc gcacgaggga    6900
gcttccaggg ggaaacgcct ggtatcttta tagtcctgtc gggtttcgcc acctctgact    6960
tgagcgtcga ttttgtgat gctcgtcagg ggggcggagc ctatgaaaaa acgccagcaa    7020
cgcggccttt ttacggttcc tggccttttg ctggcctttt gctcacatgt tctttcctgc    7080
```

```
gttatcccct gattctgtgg ataaccgtat taccgccttt gagtgagctg ataccgctcg    7140
ccgcagccga acgaccgagc gcagcgagtc agtgagcgag gaagcggaag              7190
```

<210> SEQ ID NO 16
<211> LENGTH: 40
<212> TYPE: DNA
<213> ORGANISM: Artificial Sequence
<220> FEATURE:
<223> OTHER INFORMATION: primer

<400> SEQUENCE: 16

```
ccgggcgtta ataattgttt gtaagttatt cgaaacgagg                          40
```

<210> SEQ ID NO 17
<211> LENGTH: 40
<212> TYPE: DNA
<213> ORGANISM: Artificial Sequence
<220> FEATURE:
<223> OTHER INFORMATION: primer

<400> SEQUENCE: 17

```
cctcgtttcg aataacttac aaacaattat taacgcccgg                          40
```

<210> SEQ ID NO 18
<211> LENGTH: 46
<212> TYPE: DNA
<213> ORGANISM: Artificial Sequence
<220> FEATURE:
<223> OTHER INFORMATION: primer

<400> SEQUENCE: 18

```
ctggtaaccg ggcaataatt gtttgtaaag cgttattcga aacgag                   46
```

<210> SEQ ID NO 19
<211> LENGTH: 40
<212> TYPE: DNA
<213> ORGANISM: Artificial Sequence
<220> FEATURE:
<223> OTHER INFORMATION: primer

<400> SEQUENCE: 19

```
cgctttacaa acaattattg cccggttacc aggcgaagag                          40
```

<210> SEQ ID NO 20
<211> LENGTH: 36
<212> TYPE: DNA
<213> ORGANISM: Artificial Sequence
<220> FEATURE:
<223> OTHER INFORMATION: primer

<400> SEQUENCE: 20

```
ccacggcgcg acttcatgct tcacttccag cattgc                              36
```

<210> SEQ ID NO 21
<211> LENGTH: 40
<212> TYPE: DNA
<213> ORGANISM: Artificial Sequence
<220> FEATURE:
<223> OTHER INFORMATION: primer

<400> SEQUENCE: 21

```
ctggaagtga agcatgaagt cgcgccgtgg attgatctgc                          40
```

<210> SEQ ID NO 22

<210> SEQ ID NO 22
<211> LENGTH: 36
<212> TYPE: DNA
<213> ORGANISM: Artificial Sequence
<220> FEATURE:
<223> OTHER INFORMATION: primer

<400> SEQUENCE: 22
cacggatcga agacagcatc gtgaccaaag cagacg        36

<210> SEQ ID NO 23
<211> LENGTH: 36
<212> TYPE: DNA
<213> ORGANISM: Artificial Sequence
<220> FEATURE:
<223> OTHER INFORMATION: primer

<400> SEQUENCE: 23
gctttggtca cgatgctgtc ttcgatccgt ggtatc        36

<210> SEQ ID NO 24
<211> LENGTH: 27
<212> TYPE: DNA
<213> ORGANISM: Artificial Sequence
<220> FEATURE:
<223> OTHER INFORMATION: primer

<400> SEQUENCE: 24
gactagtccg gaataatacg gttggac        27

<210> SEQ ID NO 25
<211> LENGTH: 29
<212> TYPE: DNA
<213> ORGANISM: Artificial Sequence
<220> FEATURE:
<223> OTHER INFORMATION: primer

<400> SEQUENCE: 25
ggcttctggc tgccccagat atacggtgg        29

<210> SEQ ID NO 26
<211> LENGTH: 29
<212> TYPE: DNA
<213> ORGANISM: Artificial Sequence
<220> FEATURE:
<223> OTHER INFORMATION: primer

<400> SEQUENCE: 26
ccaccgtata tctggggcag ccagaagcc        29

<210> SEQ ID NO 27
<211> LENGTH: 7163
<212> TYPE: DNA
<213> ORGANISM: Bifidobacterium longum

<400> SEQUENCE: 27
agcgcccaat acgcaaaccg cctctccccg cgcgttggcc gattcattaa tgcagctggc        60
acgacaggtt tcccgactgg aaagcgggca gtgagcgcaa cgcaattaat gtgagttagc       120
tcactcatta ggcaccccag gctttacact ttatgcttcc ggctcgtatg ttgtgtggaa       180
ttgtgagcgg ataacaattt cacacaggaa acagctatga ccatgattac gccaagcttg       240
gggagacacg acgttgacca cgttggcccc gttcattcag aaagtcgcgg tccccctcccc       300 cacacgcgca ttgggcacgt gggacaagca gctgctcaag gaactgcgag accacatcaa       360
caccataatc gatgaggaga ccgccgaatc cgccgagccg gtgacgctgg cccgcttctc       420

```
ttggcgttcg atgatcacca tgctgctggt catcgtggcc gtggtcgtgg tcttcaccca    480
actgaagccc gaggagatca tcaccgcgct gaccaacgcc aacccgttga tggcggtggt    540
gacgctcgcg ttcggtgtct gcggctggat cggctcgtcg atttcgctcg gttccctgat    600
ggcgcggcac aagcgtgaca atatgggcgt cttcatgagc caggtggcag gcggcttcgc    660
caccgtatcc atgccagccg gcgtgggccc ctcgttcgtc aacctgcagt cctgcgcaa    720
atccggctat cgcaacaccc aggcgaccgc aattatgagc gccgcgctcg tggtgtatta    780
cgccgtgtac ttctccatgc tggtcatcat cggcctgttc accggccgca acatgttctc    840
cggcgcaatc ccgacaaaca cgttggttat cgtgctgggc gttgtggtcg tggtgctgtc    900
cattgcgatg atgattccgc cgttgcgcca ctgggtgacc cgtcgtctta tgccgctggc    960
caagacgtat atcaaccagc tgctggacgt gctttcccag ccccgacagc tcacagtcag   1020
ctgcctaggc gcgctgttcc agaacgcgac cactgggctc gctttctggg cggccctgca   1080
agcgttcggc tattcatcga atccgattga aacgacgttc gtcttcctgc tggcctatgc   1140
attgggttcc gcagtgccca ctccaggcgg tctgggcggt gtggaagcgg cgctgacatt   1200
cgcgttcgtg gcggtcggag tgccgcaggg cgtggcgctt ccgccacttt gctgcaccg   1260
cgtggtgttc tactggctgc gcattccgct gggcgcggcg gccatgaagt ggcttgacaa   1320
gcataatctt gtctgattcg tctattttca tacccccttc ggggaaatag atgtgaaaac   1380
ccttataaaa cgcgggtttt cgcagaaaca tgcgctagta tcattgatga caacatggac   1440
taagcaaaag tgcttgtccc ctgacccaag aaggatgctt tatggcatac aacaagtctg   1500
acctcgtttc gaataacgct ttacaaacaa ttattaacgc ccggttacca ggcgaagagg   1560
ggctgtggca gattcatctg caggacggaa aaatcagcgc cattgatgcg caatccggcg   1620
tgatgcccat aactgaaaac agcctggatg ccgaacaagg tttagttata ccgccgtttg   1680
tggagccaca tattcacctg gacaccacgc aaaccgccgg acaaccgaac tggaatcagt   1740
ccggcacgct gtttgaaggc attgaacgct gggccgagcg caaagcgtta ttaacccatg   1800
acgatgtgaa acaacgcgca tggcaaacgc tgaaatggca gattgccaac ggcattcagc   1860
atgtgcgtac ccatgtcgat gtttcggatg caacgctaac tgcgctgaaa gcaatgctgg   1920
aagtgaagca ggaagtcgcg ccgtggattg atctgcaaat cgtcgccttc cctcaggaag   1980
ggattttgtc gtatcccaac ggtgaagcgt tgctggaaga ggcgttacgc ttaggggcag   2040
atgtagtggg ggcgattccg catttgaat ttacccgtga atacggcgtg gagtcgctgc    2100
ataaaacctt cgccctggcg caaaaatacg accgtctcat cgacgttcac tgtgatgaga   2160
tcgatgacga gcagtcgcgc tttgtcgaaa ccgttgctgc cctggcgcac catgaaggca   2220
tgggcgcgcg agtcaccgcc agccacacca cggcaatgca ctcctataac ggggcgtata   2280
cctcacgcct gttccgcttg ctgaaaatgt ccggtattaa ctttgtcgcc aacccgctgg   2340
tcaatattca tctgcaagga cgtttcgata cgtatccaaa acgtcgcggc atcacgcgcg   2400
ttaaagagat gctggagtcc ggcattaacg tctgctttgg tcacgatgct gtcttcgatc   2460
cgtggtatcc gctgggaacg cgcgaatatg ctgcaagtgct gcatatgggg ctgcatgttt   2520
gccagttgat gggctacggg cagattaacg atggcctgaa tttaatcacc caccacagcg   2580
caaggacgtt gaatttgcag gattacggca ttgccgccgg aaacagcgcc aacctgatta   2640
tcctgccggt tgaaaatggg tttgatgcgc tgcgccgtca ggttccggta cgttattcgg   2700
tacgtggcgg caaggtgatt gccagcacac aaccggcaca aaccaccgta tatctggagc   2760
```

-continued

```
agccagaagc catcgattac aaacgttgag ttaacgcctt ccaggatgtg ttcgtcgagg    2820
ctatgaagtc cggcgaaggc ctgaagctca ccggcctgtt ctccgctgag cgcgtcaagc    2880
gcccggctcg caccggccgc aacccgcgca ctggcgagca gattgacatt ccggcttcct    2940
acggcgttcg tatctccgct ggctccctgc tgaagaaggc cgtcaccgag tgaccttctg    3000
ctcgtagcga ttacttcgag cattactgac gacaaagacc ccgaccgaga tggtcggggt    3060 cttttttgttg tggtgctgtg acgtgttgtc aaccgtatt attccggact agtcggccgt    3120
acgggcccga taggcaggcc cagctcaagg cccgcgagaa cgacctcgtg gcgcggcgca    3180
gggaacgcga acgcaaggcc cgcaccaagc gcctgatcga ggtcggcgcg atggccgagt    3240
cggccgcggg cttcgaggga ggcgacgaga gggccaagga gcacatcgcc cgcctcgtgc    3300
agctcggctc cctggtggag tccctgtgct ccaccgacgt gatggccaac tacacgagcc    3360
gcgaggacct cagggccacc gtcgccaagg ctctggaaca caacgtcagg accagcgatg    3420
gcatgaactg gaacctccag gacctcgtct acgaggcgct gagcgaggaa tggcgcaaaa    3480
gggacggcga gatcagcgac ccatgggcca acgacgaggc ggacggatac cagccgccct    3540
catacgagcc ggtcaacccc gaacgcagga ctccccagac gccctccgat ggcctgatct    3600
gacgtccgaa aaaaggcgct gtgcgccctt tttaaatctt ttataaatct ttttacattc    3660
ttttagcccc tccgcagcct tactctccca acgggtttca gccgaaacct acaccaaaag    3720
gggagcgaac ctacaccaaa aggggagcga acctacacca aaggggagc gaacctacac    3780 caaaagggga gctatataca ccttttgtta tttaaggtgc aagttgtgct atgctgaggc    3840
catgtccatg agatcgtgaa gttcagcacc agttcaacaa cgtcgcgctg aagaagttcg    3900
acgccgtgca cctggacgtg ctcatggcga tcgcctcaag ggtgagggag aagggcacgg    3960
ccacggtgga gttctcgttc gaggagctgc gcggcctcat gcgattgagg aagaacctga    4020
ccaacaagca gctggccgac aagatcgtgc agacgaacgc gcgcctgctg gcgctgaact    4080
acatgttcga ggattcgggc aagatcatcc agttcgcgct gttcacgaag ttcgtcaccg    4140
acccgcagga ggcgactctc gcggttgggg tcaacgagga gttcgcgttc ctgctcaacg    4200
acctgaccag ccagttcacg cgcttcgagc tggccgagtt cgccgacctc aagagcaagt    4260
acgccaagga gttctaccgc agggccaagc agtaccgcag ctccggaatc tggaagatcg    4320
gccgcgacga gttctgccga ctgcttggcg ttccaccgtc ggcaataacc cagacacgat    4380
atctgaatca gaaggttctt cagccaattc aggaggagtg tgggcctctc cttggcctga    4440
agatcgagcg ccagtacgtg aaacgcaggc tgtcgggctt cgtgttcaca ttcgcccgcg    4500
agacccctcc ggtgatcgac gccaggcccg tggaggcgag gaagacggac ggcgacggca    4560
agggccattg gacgagcgtt gccgggtacg gcgaggtgtt cacgaccacg gcgttgttcg    4620
acgtgacggc cgcccgggct cacttcgacg gcaccgtgga ggccggggaa tgccgtttct    4680
gcgcgtttga cgcgcgcaac cgcgaacatc atgcgcggaa cgccggaagg ctgttctagc    4740
ggccgtgtcc gcgcctctgg ggcggttgcg cctgccatgg gtcgatctgc cgctgttcgg    4800
cctcacgctg gtctgtgcgc tgcctgatct ccctgagcag gtcggccttg gtcctggggg    4860
cgcttcgctc ctcgaacggg ccgctctccc ccaggtcctc gggctcgctc aggtccaacg    4920
gctcgtcacc ggacggctcg ggccggttct ctccctgtgc cgggttctcc gcctgtgcgc    4980
gttgttcggc catgcgcagt gcgagggcct tcacctgttc ggggcttagt acttgcatgc    5040
ctgcaggtcg attttcgttc gtgaatacat gttataataa ctataactaa taacgtaacg    5100
tgactggcaa gagatatttt taaaacaatg aataggttta cacttacttt agttttatgg    5160
```

-continued

```
aaatgaaaga tcatatcata tataatctag aataaaatta actaaaataa ttattatcta      5220
gataaaaaat ttagaagcca atgaaatcta taaataaact aaattaagtt tatttaatta      5280
acaactatgg atataaaata ggtactaatc aaaatagtga ggaggatata tttgaataca      5340
tacgaacaaa ttaataaagt gaaaaaaata cttcggagac atttaaaaaa taaccttatt      5400
ggtacttaca tgtttggatc aggagttgag agtggaccaa aaccaaatag tgatcttgac      5460
tttttagtcg tcgtatctga accattgaca gatcaaagta aagaaatact tatacaaaaa      5520
attagaccta tttcaaaaaa aataggagat aaaagcaact tacgatatat cgaattaacg      5580
attattattc agcaagaaat ggtaccgtgg aatcatcctc ccaaacaaga atttatttat      5640
ggagaatggt tacaagagct ttatgaacaa ggatacattc ctcagaagga attaaattca      5700
gatttaacca taatgcttta ccaagcaaaa cgaaaaaata aaagaatata cggaaattat      5760
gacttagagg aattactacc tgatattcca tttttctgatg tgagaagagc cattatggat      5820
tcgtcagagg aattaataga taattatcag gatgatgaaa ccaactctat attaacttta      5880
tgccgtatga ttttaactat ggacacgggt aaaatcatac caaaagatat tgcgggaaat      5940
gcagtggctg aatcttctcc attagaacat agggagagaa ttttgttagc agttcgtagt      6000
tatcttggag agaatattga atggactaat gaaaatgtaa atttaactat aaactattta      6060
aataacagat taaaaaaatt ataaaaaaat tgaaaaaatg gtggaaacac ttttttcaat      6120
ttttttgttt tattatttaa tggggacccc gagtcaggca actatggatg aacgaaatag      6180
acagatcgct gagataggtg cctcactgat taagcattgg taactgtcag accaagttta      6240
ctcatatata ctttagattg atttaaaact tcattttaaa tttaaaagga tctaggtgaa      6300
gatccttttt gataatctca tgaccaaaat cccttaacgt gagttttcgt tccactgagc      6360
gtcagacccc gtagaaaaga tcaaaggatc ttcttgagat cctttttttc tgcgcgtaat      6420
ctgctgcttg caaacaaaaa aaccaccgct accagcggtg gtttgtttgc cggatcaaga      6480
gctaccaact ctttttccga aggtaactgg cttcagcaga gcgcagatac caaatactgt      6540
ccttctagtg tagccgtagt taggccacca cttcaagaac tctgtagcac cgcctacata      6600
cctcgctctg ctaatcctgt taccagtggc tgctgccagt ggcgataagt cgtgtcttac      6660
cgggttggac tcaagacgat agttaccgga taaggcgcag cggtcgggct gaacggggg       6720 ttcgtgcaca cagcccagct tggagcgaac gacctacacc gaactgagat acctacagcg      6780
tgagctatga gaaagcgcca cgcttcccga agggagaaag gcggacaggt atccggtaag      6840
cggcagggtc ggaacaggag agcgcacgag ggagcttcca gggggaaacg cctggtatct      6900
ttatagtcct gtcgggtttc gccacctctg acttgagcgt cgatttttgt gatgctcgtc      6960
aggggggcgg agcctatgga aaaacgccag caacgcggcc ttttacggt tcctggcctt       7020 ttgctggcct tttgctcaca tgttctttcc tgcgttatcc cctgattctg tggataaccg      7080
tattaccgcc tttgagtgag ctgataccgc tcgccgcagc cgaacgaccg agcgcagcga      7140
gtcagtgagc gaggaagcgg aag                                              7163
```

<210> SEQ ID NO 28
<211> LENGTH: 427
<212> TYPE: PRT
<213> ORGANISM: Escherichia coli

<400> SEQUENCE: 28

Met Ser Asn Asn Ala Leu Gln Thr Ile Ile Asn Ala Arg Leu Pro Gly
1               5                   10                  15

Glu Glu Gly Leu Trp Gln Ile His Leu Gln Asp Gly Lys Ile Ser Ala
            20                  25                  30

Ile Asp Ala Gln Ser Gly Val Met Pro Ile Thr Glu Asn Ser Leu Asp
        35                  40                  45

Ala Glu Gln Gly Leu Val Ile Pro Pro Phe Val Glu Pro His Ile His
50                  55                  60

Leu Asp Thr Thr Gln Thr Ala Gly Gln Pro Asn Trp Asn Gln Ser Gly
65                  70                  75                  80

Thr Leu Phe Glu Gly Ile Glu Arg Trp Ala Glu Arg Lys Ala Leu Leu
                85                  90                  95

Thr His Asp Asp Val Lys Gln Arg Ala Trp Gln Thr Leu Lys Trp Gln
            100                 105                 110

Ile Ala Asn Gly Ile Gln His Val Arg Thr His Val Asp Val Ser Asp
        115                 120                 125

Ala Thr Leu Thr Ala Leu Lys Ala Met Leu Glu Val Lys Gln Glu Val
130                 135                 140

Ala Pro Trp Ile Asp Leu Gln Ile Val Ala Phe Pro Gln Glu Gly Ile
145                 150                 155                 160

Leu Ser Tyr Pro Asn Gly Glu Ala Leu Leu Glu Glu Ala Leu Arg Leu
                165                 170                 175

Gly Ala Asp Val Val Gly Ala Ile Pro His Phe Glu Phe Thr Arg Glu
            180                 185                 190

Tyr Gly Val Glu Ser Leu His Lys Thr Phe Ala Leu Ala Gln Lys Tyr
        195                 200                 205

Asp Arg Leu Ile Asp Val His Cys Asp Glu Ile Asp Asp Glu Gln Ser
210                 215                 220

Arg Phe Val Glu Thr Val Ala Ala Leu Ala His His Glu Gly Met Gly
225                 230                 235                 240

Ala Arg Val Thr Ala Ser His Thr Thr Ala Met His Ser Tyr Asn Gly
                245                 250                 255

Ala Tyr Thr Ser Arg Leu Phe Arg Leu Leu Lys Met Ser Gly Ile Asn
            260                 265                 270

Phe Val Ala Asn Pro Leu Val Asn Ile His Leu Gln Gly Arg Phe Asp
        275                 280                 285

Thr Tyr Pro Lys Arg Arg Gly Ile Thr Arg Val Lys Glu Met Leu Glu
290                 295                 300

Ser Gly Ile Asn Val Cys Phe Gly His Asp Asp Val Phe Asp Pro Trp
305                 310                 315                 320

Tyr Pro Leu Gly Thr Ala Asn Met Leu Gln Val Leu His Met Gly Leu
                325                 330                 335

His Val Cys Gln Leu Met Gly Tyr Gly Gln Ile Asn Asp Gly Leu Asn
            340                 345                 350

Leu Ile Thr His His Ser Ala Arg Thr Leu Asn Leu Gln Asp Tyr Gly
        355                 360                 365

Ile Ala Ala Gly Asn Ser Ala Asn Leu Ile Ile Leu Pro Ala Glu Asn
370                 375                 380

Gly Phe Asp Ala Leu Arg Arg Gln Val Pro Val Arg Tyr Ser Val Arg
385                 390                 395                 400

Gly Gly Lys Val Ile Ala Ser Thr Gln Pro Ala Gln Thr Thr Val Tyr
                405                 410                 415

Leu Glu Gln Pro Glu Ala Ile Asp Tyr Lys Arg
            420                 425

```
<210> SEQ ID NO 29
<211> LENGTH: 18
<212> TYPE: PRT
<213> ORGANISM: Bifidobacterium longum

<400> SEQUENCE: 29

Met Ala Tyr Asn Lys Ser Asp Leu Val Ser Lys Ile Ala Gln Lys Ser
1               5                   10                  15

Asn Leu
```